United States Patent
Bucholz

(10) Patent No.: US 6,678,545 B2
(45) Date of Patent: *Jan. 13, 2004

(54) SYSTEM FOR DETERMINING THE POSITION IN A SCAN IMAGE CORRESPONDING TO THE POSITION OF AN IMAGING PROBE

(75) Inventor: Richard D. Bucholz, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/197,337

(22) Filed: Jul. 16, 2002

(65) Prior Publication Data

US 2002/0183615 A1 Dec. 5, 2002

Related U.S. Application Data

(63) Continuation of application No. 09/151,798, filed on Sep. 22, 1998, now Pat. No. 6,463,319, which is a continuation of application No. 08/543,516, filed on Oct. 16, 1995, now Pat. No. 5,851,183, which is a continuation of application No. 07/858,980, filed on May 15, 1992, now abandoned, which is a continuation-in-part of application No. 07/600,753, filed on Oct. 19, 1990, now abandoned.

(51) Int. Cl.[7] .................................................. A61B 6/00

(52) U.S. Cl. ...................... 600/426; 600/427; 600/429; 606/130

(58) Field of Search ................................ 600/407, 426, 600/427, 429, 425, 424, 437, 439, 443; 606/130

(56) References Cited

U.S. PATENT DOCUMENTS 3,821,469 A 6/1974 Whetstone et al.
3,868,565 A 2/1975 Kuipers
3,963,028 A 6/1976 Cooley et al.
3,983,474 A 9/1976 Kuipers
4,058,114 A 11/1977 Soldner
4,068,156 A 1/1978 Johnson et al.
4,117,337 A 9/1978 Staats
4,182,312 A 1/1980 Mushabac
4,209,254 A 6/1980 Reymond (List continued on next page.)

FOREIGN PATENT DOCUMENTS

DE 2534516 2/1976
DE 2852949 6/1980

(List continued on next page.)

OTHER PUBLICATIONS

Cinquin et al., "Computer Assisted Medical Interventions," The 1st Workshop on Domestic Robotics—The 2nd Workshop on Medical & Healthcare Robotics, Sep. 5–7, 1989, pp. 63–65.

Cinquin et al., "IGOR: Image Guided Operating Robot, Methodololgy, Applications," IEEE EMBS, Paris, 1992, pp. 1–2.

(List continued on next page.)

Primary Examiner—Ruth S. Smith
(74) Attorney, Agent, or Firm—Senniger, Powers, Leavitt & Roedel

(57) ABSTRACT

A system for use in imaging a subject and determining a position relative to a body of a patient. A base is fixed in relation to the subject. An imaging probe is configured to scan the subject and provide scan images of the subject. An array of receivers is in communication with the base and the imaging probe. A first plurality of reference points is fixed in relation to the base and in communication with the array. A second plurality of reference points is fixed in relation to the imaging probe and in communication with the array. A processor in communication with the imaging probe and the array calculates the position in the scan images corresponding to the position of the imaging probe relative to the subject.

32 Claims, 9 Drawing Sheets

U.S. PATENT DOCUMENTS

| | | |
|---|---|---|
| 4,262,306 A | 4/1981 | Renner |
| 4,341,220 A | 7/1982 | Perry |
| 4,358,856 A | 11/1982 | Stivender et al. |
| 4,368,556 A | 1/1983 | Wanner et al. |
| 4,396,945 A | 8/1983 | DiMatteo et al. |
| 4,407,298 A | 10/1983 | Lentz et al. |
| 4,419,012 A | 12/1983 | Stephensons |
| 4,457,311 A | 7/1984 | Sorenson et al. |
| 4,465,069 A | 8/1984 | Barbier et al. |
| 4,473,074 A | 9/1984 | Vassiliadis |
| 4,506,676 A | 3/1985 | Duska |
| 4,571,834 A | 2/1986 | Fraser et al. |
| 4,583,538 A | 4/1986 | Onik et al. |
| 4,585,350 A | 4/1986 | Pryer et al. |
| 4,592,352 A | 6/1986 | Patil |
| 4,602,622 A | 7/1986 | Bär et al. |
| 4,608,977 A | 9/1986 | Brown |
| 4,638,798 A | 1/1987 | Sheldon et al. |
| 4,649,504 A | 3/1987 | Krouglicof et al. |
| 4,651,732 A | 3/1987 | Frederick |
| 4,659,971 A | 4/1987 | Suzuki et al. |
| 4,660,970 A | 4/1987 | Ferrano |
| 4,672,306 A | 6/1987 | Thong |
| 4,673,352 A | 6/1987 | Hansen |
| 4,674,057 A | 6/1987 | Caughman et al. |
| D291,246 S | 8/1987 | Lower |
| 4,686,997 A | 8/1987 | Oloff et al. |
| 4,698,777 A | 10/1987 | Toyoda et al. |
| 4,701,047 A | 10/1987 | Eibert et al. |
| 4,701,049 A | 10/1987 | Beckmann et al. |
| 4,701,407 A | 10/1987 | Seppel |
| 4,705,395 A | 11/1987 | Hageniers |
| 4,705,401 A | 11/1987 | Addleman |
| 4,706,665 A | 11/1987 | Gouda |
| 4,709,156 A | 11/1987 | Murphy et al. |
| 4,721,384 A | 1/1988 | Dietrich et al. |
| 4,721,388 A | 1/1988 | Takagi et al. |
| 4,722,056 A | 1/1988 | Roberts et al. |
| 4,723,544 A | 2/1988 | Moore et al. |
| 4,727,565 A | 2/1988 | Ericson |
| 4,733,661 A | 3/1988 | Palestrant |
| 4,733,662 A | 3/1988 | DeSatnick et al. |
| 4,733,969 A | 3/1988 | Case et al. |
| 4,737,032 A | 4/1988 | Addleman et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines |
| 4,761,072 A | 8/1988 | Pryor |
| 4,762,016 A | 8/1988 | Stoughton et al. |
| 4,764,015 A | 8/1988 | Bieringer et al. |
| 4,764,016 A | 8/1988 | Johansson |
| 4,767,934 A | 8/1988 | Stauffer |
| 4,775,235 A | 10/1988 | Hecker et al. |
| 4,776,749 A | 10/1988 | Wanzenberg et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,803,645 A | 2/1989 | Ohtomo et al. |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,822,163 A | 4/1989 | Schmidt |
| 4,825,091 A | 4/1989 | Breyer et al. |
| 4,829,373 A | 5/1989 | Leberl et al. |
| 4,835,710 A | 5/1989 | Schnelle et al. |
| 4,836,778 A | 6/1989 | Baumrind et al. |
| 4,837,669 A | 6/1989 | Tharp et al. |
| 4,841,967 A | 6/1989 | Chang et al. |
| 4,875,478 A | 10/1989 | Chen |
| 4,896,673 A | 1/1990 | Rose et al. |
| 4,931,056 A | 6/1990 | Ghajar et al. |
| 4,933,843 A | 6/1990 | Scheller et al. |
| 4,943,296 A | 7/1990 | Funakubo et al. |
| 4,945,914 A | 8/1990 | Allen |
| 4,955,891 A | 9/1990 | Carol |
| 4,961,422 A | 10/1990 | Marchosky |
| 4,982,188 A | 1/1991 | Fodale et al. |
| 4,991,579 A | 2/1991 | Allen |
| 5,005,142 A | 4/1991 | Lipchak et al. |
| 5,016,639 A | 5/1991 | Allen |
| 5,017,139 A | 5/1991 | Mushabac |
| 5,027,810 A | 7/1991 | Patureau et al. |
| 5,027,818 A | 7/1991 | Bova et al. |
| 5,039,867 A | 8/1991 | Nishihara et al. |
| 5,047,036 A | 9/1991 | Koutrouvelis |
| 5,050,608 A | 9/1991 | Watanabe et al. |
| 5,059,789 A | 10/1991 | Salcudean et al. |
| 5,078,142 A | 1/1992 | Siczek et al. |
| 5,079,699 A | 1/1992 | Tuy et al. |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,099,846 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,178,164 A | 1/1993 | Allen |
| 5,186,174 A | 2/1993 | Schlöndorff et al. |
| 5,193,106 A | 3/1993 | DeSena |
| 5,197,476 A | 3/1993 | Nowacki et al. |
| 5,198,877 A | 3/1993 | Schulz |
| 5,211,164 A | 5/1993 | Allen |
| 5,222,499 A | 6/1993 | Allen et al. |
| 5,224,049 A | 6/1993 | Mushabac |
| 5,230,338 A | 7/1993 | Allen et al. |
| 5,249,581 A | 10/1993 | Horbal et al. |
| 5,251,127 A | 10/1993 | Raab |
| 5,257,998 A | 11/1993 | Ota et al. |
| 5,261,404 A | 11/1993 | Mick et al. |
| 5,279,309 A | 1/1994 | Taylor et al. |
| 5,291,889 A | 3/1994 | Kenet et al. |
| 5,295,200 A | 3/1994 | Boyer |
| 5,295,483 A | 3/1994 | Nowacki et al. |
| 5,299,288 A | 3/1994 | Glassman et al. |
| 5,305,203 A | 4/1994 | Raab |
| 5,309,913 A | 5/1994 | Kormos et al. |
| D349,573 S | 8/1994 | Bookwalter et al. |
| 5,355,129 A | 10/1994 | Baumann |
| D353,668 S | 12/1994 | Banks et al. |
| 5,383,454 A | 1/1995 | Bucholz |
| D357,534 S | 4/1995 | Hayes |
| D359,557 S | 6/1995 | Hayes |
| 5,494,034 A | 2/1996 | Schlondorff et al. |
| 5,531,520 A | 7/1996 | Grimson et al. |
| 5,622,170 A | 4/1997 | Schulz |
| 5,638,819 A | 6/1997 | Manwaring et al. |
| 5,662,111 A | 9/1997 | Cosman |
| 5,682,886 A | 11/1997 | Delp et al. |
| 5,848,967 A | 12/1998 | Cosman |
| 6,463,319 B1 * | 10/2002 | Bucholz .................... 600/426 |

FOREIGN PATENT DOCUMENTS

| | | |
|---|---|---|
| DE | 3205085 | 9/1982 |
| DE | 3508730 | 9/1986 |

| | | |
|---|---|---|
| DE | 8701668 | 5/1987 |
| DE | 3205915 | 9/1993 |
| EP | 0 018 166 | 4/1980 |
| EP | 0 062 941 | 10/1982 |
| EP | 0 155 857 | 1/1985 |
| EP | 0 207 452 | 1/1987 |
| EP | 0 322 363 | 6/1989 |
| EP | 0 427 358 | 10/1990 |
| EP | 0 456 103 | 5/1991 |
| EP | 0 359 773 | 10/1993 |
| EP | 0 326 768 | 12/1998 |
| FR | 2 417 970 | 10/1979 |
| GB | 2094590 | 2/1982 |
| JP | 62-000327 | 1/1987 |
| JP | 62-74385 | 3/1987 |
| WO | WO 88/09151 | 12/1988 |
| WO | WO 90/05494 | 5/1990 |
| WO | WO 91/04711 | 4/1991 |
| WO | WO 91/07726 | 5/1991 |
| WO | WO 92/00702 | 7/1991 |
| WO | WO 92/06645 A1 | 4/1992 |

OTHER PUBLICATIONS

Cinquin et al., "IGOR: Image Guided Robot. Methodology, Applications," IEEE EMBS (1992).

Dever et al., "OR Role Seen for 3–D Imaging," Radiology Today, Feb. 1991, 2 pages.

Foley et al., "Image–Guided Intraoperative Spinal Localization," Intraoperative Neuroprotection, Chapter 19, 1996, pp. 325–340.

Friets et al., "A Frameless Sterotaxic Operating Microscope for Neurosurgery," IEEE Transactions on Biomedical Engineering, vol. 36, No. 6, Jun. 1989, pp. 608, 613–617.

Gildenberg et al., "Calculation of Stereotactic Coordinates from the Computed Tomographic Scan," Neurosurgery, vol. 10, No. 5, May 1982, pp. 580–586.

Glaser et al., "The Image–Combining Computer Microscope—an Interactive Instrument for Morphometry of the Nervous System," Journal of Neuroscience Methods, vol. 8, 1983, pp. 17–32.

Gleason et al., "Stereotactic Localization (with Computerized Tomographic Scanning), Biopsy, and Radiofrequency Treatment of Deep Brain Lesions," Neurosurgery, vol. 2, No. 3, 1978, pp. 217–222.

Gomez et al., "Transcranial Doppler Ultrasound Following Closed Head Injury: Vasospasm or Vasoparalysis?," Surg. Neurol., vol. 35, No. 1, Jan. 1991, pp. 30–35.

Gonzalez et al., "Digital Image Processing," Second Edition, Addison–Wesley Publishing Company, 1987, pp. 52–54.

Gouda et al., "New Frame for Stereotaxic Surgery," J. Neurosurg, vol. 53, Aug. 1980, pp. 256–259.

Greitz, et al., "Head Fixation System for Interation of Radiodiagnostic and Therapeutic Procedures," Neuroradiology, vol. 19, No. 1, 1980, pp. 1–6.

Bergstrom, et al., "Stereotaxic Computed Tomography," Am. J. Roentgenol, 127:167–170, 1976, pp. 167–170.

Birg, et al., "A Computer Programme System for Stereotactic Neurosurgery," Acta Neurochirurgica Suppl., 24, 1977, 99–108.

Boëthius et al., "Stereotaxic Computerized Tomography with a GE 8800 Scanner," J. Neurosurg, vol. 52, Jun. 1980, pp. 794–800.

Boethius et al., "Stereotactic Biopsies and Computer Tomography in Gliomas," Acta Neurochirurgica, vol. 40, Fasc. 3–4, 1978, pp. 223–232.

Brown, "A Computeried Tomography–Computer Graphics Approach to Stereotaxic Localization," J. Neurosurg, vol. 50, No. 6, 1979, pp. 715–720.

Brown, "A Stereotactic Head Frame for Use with CT Body Scanners," Inv. Radiol., vol. 14, No. 4, Jul. 1979, pp. 300–304.

Bullard et al., "C.T.–Guided Stereotactic Biopsies Using a Modified Frame and Gildenberg Techniques," Neurology, Neurosurgery, and Psychiatry, vol. 47, 1984, pp. 590–595.

Byte Magazine, "3–D Digitizer Captures the World," 1990, p.43.

Castleman, "Digital Image Processing," Prentice Hall, Inc., p. 364–369 (1979).

Champleboux et al., "Accurate Calibration of Cameras and Range Imaging Sensors: the NPBS Method," 1992, 6 pages.

Champleboux, "Ulilisation De Fonctions Splines Pour La Mise Au Poit d'Un Capteur Tridimension Sans Contact," Theses, Docteur de L'Univerite' Joseph Fourie Grenoble, 1991.

Adams et al., "Medical Imaging. Computer–Assisted Surgery," IEEE Computer Graphics & Applications, 1990, pp. 43–51.

Adams et al., "Aide Au Reperage Tridimensionnel Pour La Chirurgie De La Base Du Crane," Innov. Tech. Biol. Med., vol. 13, No. 4, pp. 409–424 (1992).

Adams et al., "Computer–Assisted Surgery," Medical Imaging, IEEE, pp. 43–51 (May 1990).

Afshar et al., "A Three–Dimensional Reconstruction of the Human Brain Stem," J. Neurosurg., vol. 57, No. 4, Oct. 1982, pp. 491–495.

Apuzzo et al., "Computed Tomographic Guidance Stereotaxis in the Management of Intracranial Mass Lesions," Neurosurgery, vol. 12, No. 3, 1983, pp. 277–285.

Arun et al., "Transactions on Pattern Analysis and Machine Intelligence," IEEE, vol. PAMI–9, No. 5, 1987, pp. 698–770.

Awwad et al., "Post–Traumatic Spinal Synovial Cyst with Spondylolysis CT Features," Journal of Computer Assisted Tomography, vol. 13, No. 2, Mar./Apr. 1989, pp. 334–337.

Awwad et al., "MR Imaging of Lumbar Juxtaarticular Cysts," Journal of Computer Assisted Tomography, vol. 14, No. 3, May/Jun. 1990, pp 415–417.

Bajcsy et al, "Computerized Anatomy Atlas of the Human Brain," Proceedings of the Second Annual Conference & Exhibition of the National Computer Graphics Association, Inc., 1981, pp. 435–441.

Batnitzky, et al., "Three–Dimensional Computer Reconstructions of Brain Lesions from Surface Contours Provided by Computed Tomography: A Prospectus," Neurosurgery, vol. 11, No. 1, Jul. 1982, pp. 73–84.

Van Buren et al., "A Multipurpose CT–Guided Stereotactic Instrument of Simple Design," Applied Neurophysiology, Jan.–Aug. 1983, pp. 211–216.

Watanabe et al., "Three Dimensional Digitizer (Neuronavigator): New Equipment for Computed Tomography–Guided Stereotaxic Surgery," 27 Surg. Neurol, 1987, pp. 543–547.

Watanabe, "Neuronavigator," Igaku–no–Ayumi, vol. 137, No. 6, May 10, 1986 (With Translation).

Wolfe, "The Infrared Handbook,", Office of Naval Research, Department of the Navy, Washington, D.C., pp. 22–63 through 22–77 (1978).

Yeates et al., "Simplified and Accurate CT–Guided Needle Biopsy of Central Nervous System Lesions," Journal of Neurosurgery, vol. 57, No. 3, Sep. 1982, pp. 390–393.

Yosugi et al., "An Articulated Neurosurgical Navigation System Using MRI and CT Images," (Feb. 1988) pp. 147–152.

Rosenbaum et al., "Computerized Tomography Guided Stereotaxis: A New Approach," Applied Neurophysiology, vol. 43, No. 3–5, Jan. 1980, pp. 172–173.

Sautot et al., "Computer Assisted Spine Surgery: A First Step Toward Clinical Application in Orthopaedics," IEEE, 1992.

Scarabin et al., "Stereotaxic Exploration in 200 Supratentorial Brain Tumors," Neuroradiology, vol. 16, Jun. 4–10, 1978, pp. 591–593.

Shelden et al., "Development of a Computerized Microstereotaxic Method for Localization and Removal of Minute CNS Lesions Under Direct 3–D Vision," J. Neurosurg, vol. 52, Jan. 1980, pp. 21–27.

Shiu et al., "Finding the Mounting Position of a Sensor by Solving a Homogeneous Transform Equation of Form AX=XB," IEEE, vol. 3, 1987, pp. 1666–1671.

Smith et al., "Multimodality Image Analysis and Display Methods for Improved Tumor Localization in Stereotactic Neurosurgery," Annual Conference for the IEEE Engineering in Medicine and Biology Society, vol. 13, No. 1, 1991, p. 210.

Valentino et al., "Three–Dimensional Visualization of Human Brain Structure–Function Relationships," The Journal of Nuclear Medicine, 1989, Posterboard 1136, vol. 30, No. 10, p. 1747.

Pixsys, Inc., "SACDAC User's Guide, Version 2e," Mar. 1989, pp. 0–1 through 5–3.

Pixsys, Inc., "Design Aide" Mar. 1989, 5 unnumbered pages.

Pixsys, Inc., "Offset Probe for Science Accessories' GP–8–3D digitizer" (Dec. 1987), one page.

Reinhardt et al., "CT–Guided 'Real Time' Stereotaxy," Acta Neurochirurgica Suppl. 46, 1989, 107–108.

Reinhardt et al., "A Computer Assisted Device for the Intra Operate CT–Correlated Localization of Brain Tumors," 1988 Eur. Surg. Res. 20:52–58.

Reinhardt et al., "Mikrochirugicshe Entfurnung tifliegender Gefaβmiβbildungen mit Hilfe der Sonar–Stereometrie," Ultraschall in Med. 12, 1991, pp. 80–84.

Reinhardt,"Surgery of Brain Neoplasms Using 32–P Tumor Marker" Acta Neurochir, 1989, 97:89–94.

Reinhardt, "Sonic Stereometry in Microsurgical Procedures for Deep–Seated Brain Tumors and Vascular Malformations," Neurosurgery, vol. 32, No. 1, Jan. 1993, pp. 51–57.

Reinhardt et al., "Interactive Sonar–Operated Device for Stereotactic and Open Surgery," Stereotac Funct Neurosurg, 1990, 54+55:393–397.

Roberts et al., "A Frameless Sterotaxic Integration of Computerized Tomographic Imaging and the Operating Microscope," J. Neurosurg., vol. 65, Oct. 1986, pp. 545–549.

O'Leary et al., "Localization of Vertex Lesions Seen on CT Scan," 1978, pp. 71–74.

Patil, "Computed Tomography Plane of the Target Approach in Computed Tomographic Stereotaxis," Neurosurgery, vol. 15, No. 3, Sep. 1984, pp. 410–414.

Paul et al., "Development of a Surgical Robot for Cementless Total Hip Arthroplasty," Clinical Orthopaedics, No. 285, Dec. 1992, pp. 57–66.

Pelizzari et al., "Accurate Three–Dimensional Registration of CT, PET and/or MR Images of the Brain," Journal of Computer Assisted Tomography, 13(1):20–26, Jan./Feb. 1989, pp. 20–26.

Pelizzari et al., 3D Patient/Image Registration: Application to Radiation Treatment Planning, Medical Physics, vol. 18, No. 3, May/Jun. 1991, p. 612.

Pelizzari et al., "Three Dimensional Correlation of PET, CT and MRI Images," The Journal of Nuclear Medicine, Abstract Book, 34th Annual Meeting, vol. 28, No. 4, Poster Session No. 528, 1987, p. 682.

Pelizzari et al., "Interactive 3D Patient–Image Registration," Lecture Notes in Computer Science, Springer–Verlag, Wye, UK, Information Procession in Medical Imaging, Proceedings, pp. 132–141 (Jul. 1991).

Penn et al., "Stereotactic Surgery with Image Processing of Computerized Tomographics Scans," Neurosurgery, vol. 3, No. 2, Sep./Oct. 1978, pp. 157–163.

Perry et al., "Computed Tomography–Guided Stereotactic Surgery: Conception and Development of a New Stereotactic Methodology," Neurosurgery, vol. 7, No. 4, Oct. 1980, pp. 376–381.

Picard et al., "The First Human Stereotaxic Apparatus," J. Neurosurg., vol. 59, Oct. 1983, pp. 673–676.

Piskun et al., "A Simplified Method of CT Assisted Localization and Biopsy of Intracranial Lesions," Surgical Neurology, vol. 11, Jun. 1979, pp. 413–417.

Mackay et al., "Computed Tomography–Directed Stereotaxy for Biopsy and Interstitial Irradiation of Brain Tumors: Technical Note," Neurosurgery, vol. 11, No. 1, 1982, pp. 38–42.

Maroon et al., "Intracranial Biopsy Assisted by Computerized Tomography," J. Neurosurg., vol. 46, No. 6, Jun. 1977, pp. 740–744.

Mazier et al., "Computer Assisted Interventionist Imaging: Application to the Vertebral Column Surgery," IEEE, vol. 12, No. 1, 1990, pp. 430–431.

Mazier et al., "Computer Assisted Vertebral Column Surgery: Application to the Spinal Pedicle Fixation," Innov. Tech. Biol. Med., vol. 11, No. 5, 1990, pp. 559–565.

Mazier et al., "Chirurgie De La Colonne Vertebrale Assiste Par Ordinateur: Application Au Vissage Pediculaire," Innov. Tech. Biol. Med., vol. 11, No. 5, pp. 559–566, 1990.

Mesqui et al., "Real–Time, Noninvasive Recording and Three–Dimensional Display of the Functional Movements of an Arbitrary Mandible Point," Proceedings, vol. 602, Biostereometrics '85, Dec. 3–6, 1985, Cannes, France, SPIE, vol. 602, pp. 77–84.

Moran et al., "Central Nervous System Lesions Biopsied or Treated by CT–guided Needle Placement," Radiology, vol. 131, No. 3, Jun. 1979 pp, 681–686.

Mosages et al., "A New Imaging Method for Intraoperative Therapy control in Skull–Base Surgery," 1988.

Mundinger et al., "Computer–Assisted Stereotactic Brain Operations by Means Including Computerized Axial Tomography," Applied Neurophysiology, vol. 41, No. 1–4, 1978, pp. 169–182.

Mundinger et al., "Treatment of Small Cerebral Gliomas with CT–Aided Stereotaxic Curietherapy," Neuroradiology, vol. 16, 1978, pp. 564–567.

Norman et al., "Localization with the EMI Scanner," The American Journal fo Roentgenology, Radium Therapy and Nuclear Medicine, vol. 125, No. 4, Dec. 1975, pp. 961–964.

Lavalee et al, "Computer Assisted Medial Interventions," NATO AISI vol. F60, 1990, pp. 301–312.

Lavalee et al., "Ponction Assistee Par Ordinateur" ("Computer Assisted Puncture"), afcet INRIA, 1987, pp. 439–449.

Lavalee et al., "Matching 3–D Smooth Surfaces with Their 2–D Projections Using 3–D Distance Maps," SPIE, vol. 1570, Geometric Methods in Computer Vision, 1991, pp. 322–336.

Lavalee, "A New System for Computer Assisted Neurosurgery," IEEE Engineering in Medicine & Biology Society 11th Annual International Conference, 1989.

Lavalee et al., "Computer Assisted Driving of a Needle into the Brain," Computer Assisted Radiology 1989, pp. 416–420.

Lavalee et al., "Computer Assisted Puncture," pp. 439–449 (Nov. 16–20, 1987).

Leksell et al., "Stereotaxis and Tomography, a Technical Note," Acta Neurrochirurgica, vol. 52, Fasc 1–2, 1980, pp. 1–7.

Lemke, et al., "Computer Assisted Driving of a Needle into the Brain," Computer Assisted Radiology Magazine, pp. 416–420 (1989).

Levin et al., "Multimodality 3–D View of the Brain Created from MRI and PET Scans," SMRI 1989: Seventh Annual Meeting Program and Abstracts, vol. 7, Supplement 1, p. 89.

Levin et al., "The Brain: Integrated Three–Dimensional Display of MR and PET Images," Radiology, 1989, vol. 172, No. 3, pp. 783–789.

Levinthal et al., "Technique for Accurate Localization with the CT Scanner," Bulletin of the Los Angeles Neurological Societies, vol. 41, No. 1, Jan. 1976, pp. 6–8.

Lunsford, "Innovations in Stereotactic Technique Coupled with Computerized Tomography," Contemporary Neurosurgery, 1982, pp. 1–6.

Kato et al., "A Frameless, Armless Navigational System for Computer Assisted Neurosurgery" 74 J. Neurosurg., 1991, pp. 845–849.

Kaufman, "New Head–Positioning System for Use with Computed Tomographic Scanning," Neurosurgery, vol. 7, No. 2, Aug. 1980, pp. 147–149.

Kelly et al., "A Microstereotactic Approach to Deep–Seated Arteriovenous Malformations," Surgical Neurology, vol. 17, No. 4, Apr. 1982, 260–262.

Kelly et al., "Computer–Assisted Stereotaxic Laser Resection of Intra–Axial Brain Neoplasma," J. Neurosurg., vol. 64, Mar. 1976, pp. 427–439.

Kelly et al., "A Stereotactic Approach to Deep–Seated Central Nervous System Neoplasms Using the Carbon Dioxide Laser," Surgical Neurology, vol.15, No. 5, May 1981, pp. 331–334.

Kelly et al., "Stereotactic CT Scanning for the Biopsy of Intracranial Lesions and Functional Neurosurgery," Applied Neurophysiology, vol. 46, Dec. 1983, pp. 193–199.

Kelly et al., "Precision Resection of Intra–Axial CNS Lesions by CT–Based Stereotactic Craniotomy and Computer Monitored $CO_2$ Laser," Acta Neurochirurgica, vol. 68, Fasc. 1–2, 1983, pp. 1–9.

Kosugi et al., "An Articulated Neurosurgical Navigation System Using MRI and CT Images," IEEE Transaction on Biomedical Engineering, vol. 35, No. 2, Feb. 1988, pp. 147–152.

Krybus et al., "Navigation Support for Surgery by Means of Optical Position Detection," Proceedings of CAR '91, pp. 362–366.

Laitinen, "Trigeminus Stereoguide: An Instrument for Stereotactic Approach Through the Foramen Ovale and Foramen Jugulare" (1984).

Lavalee et al., "Matching of Medical Images for Computed and Robot Assisted Surgery," 2 pages, (1991).

Lavalee et al., "Computer Assisted Interventionist Imaging: The Instance of Sterotactic Brain Surgery," Medinfo, 1989, pp. 613–617.

Hahn, et al., "Needle Biopsy of Intracranial Lesions Guided by Computerized Tomography," Neurosurgery, vol. 5, No. 1, 1979, pp. 11–15.

Hanson "Robots Roll into Operating Rooms," *Insight*, Apr. 8, 1991, pp. 44–45.

Hatch, "Reference–Display System for the Integration of CT Scanning and the Operating Microscope," Proceedings of the Eleventh Annual Northeast Bioengineering Conference, Mar. 14–15, 1985, IEEE 1985, pp. 252–254; Trustees of Dartmouth College, Oct. 1984, entire thesis.

Heilbrun,"Computed Tomography–Guided Stereotactic Systems," (1983).

Heilbrun et al., "Preliminary Experience with a Brown–Roberts–Wells (BRW) Computerized Tomography Stereotaxic Guidance System," J. Neurosurg., vol. 59, Aug. 1983, pp. 217–222.

Hinck et al., "A Precise Technique for Craniotomy Localization Using Computerized Tomography," J. Neurosurg, vol. 54, No. 3, Mar. 1981, pp. 416–418.

Hoerenz, "The Operating Microscope, I., Optical Principles, Illumination Systems, and Support System," Journal of Microsurgery, vol. 2, No. 5, Mar.–Apr. 1980, pp. 364–369.

Holman et al., "Computer–Assisted Superimposition of Magnetic Resonance and High–Resolution Technetium–99–m–HMPAO and Thallium–201 SPECT Images of the Brain," The Journal of Nuclear Medicine, vol. 32, No. 8, Aug. 1991, pp. 1478–1484.

Horner et al., "A Comparison of CT–Stereotaxic Brain Biopsy Techniques," Investigative Radiology, vol. 19, Sep.–Oct. 1984, pp. 367–373.

Hounsfield, "Computerized Transverse Axial Scanning (Tomography): Part 1, Description of System," British Journal of Radiology, vol. 46, 1973, pp. 1016–1022.

Jacques et al., "Computerized Three–Dimensional Stereotaxic Removal of Small Central Nervous System Lesions in Patients," J. Neurosurg. vol. 53, No. 6, Dec. 1980, pp. 816–820.

Jacques et al., "A Computerized Microstereotactic Method to Approach, 3–Dimensionally Reconstruct, Remove and Adjuvantly Treat Small CNS Lesions," Appl. Neurophysiology 1980, 43:176–182.

\* cited by examiner

SCANNED IMAGE
COORDINATE SYSTEM

SURGICAL PROBE
COORDINATE SYSTEM

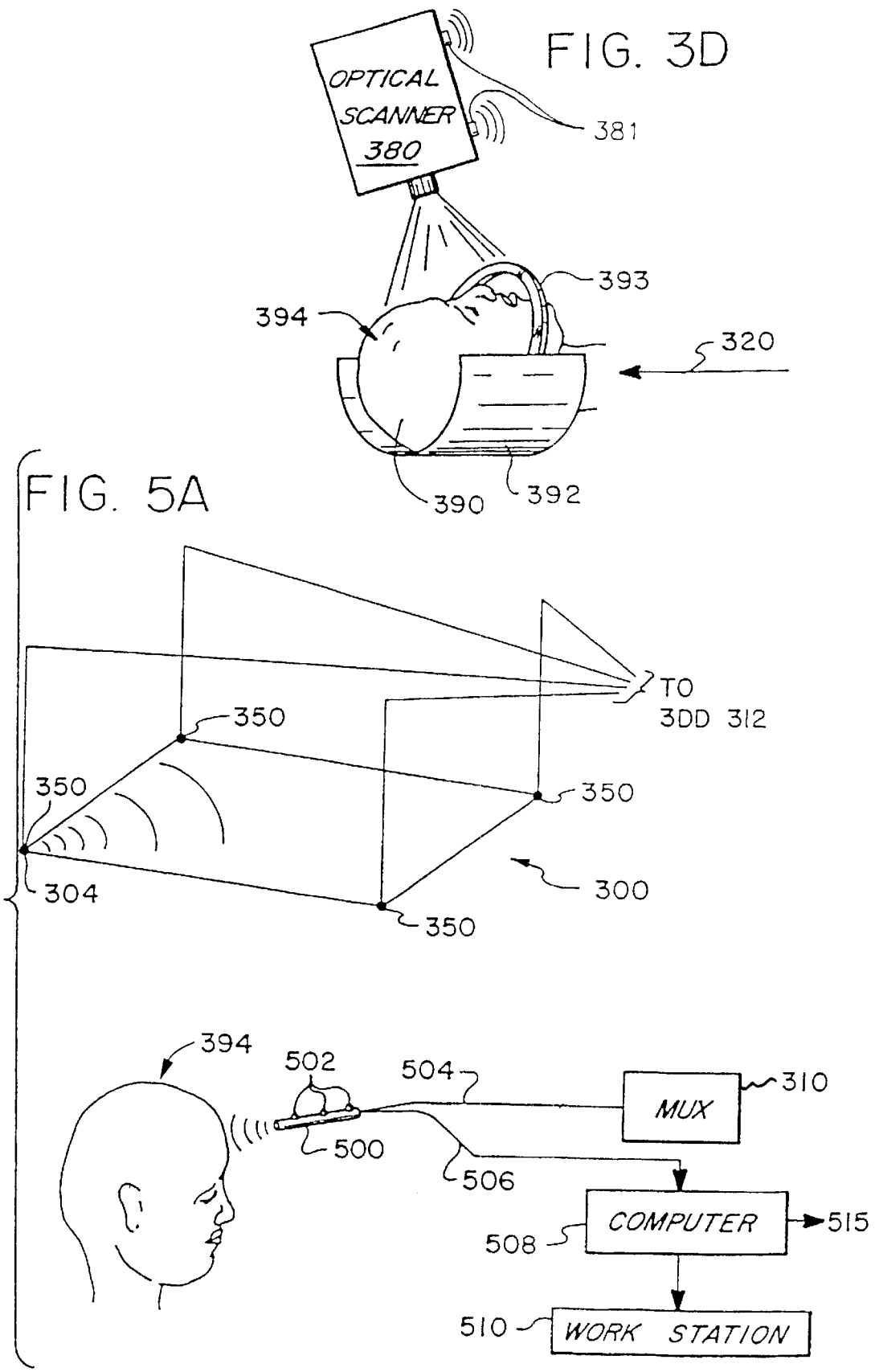

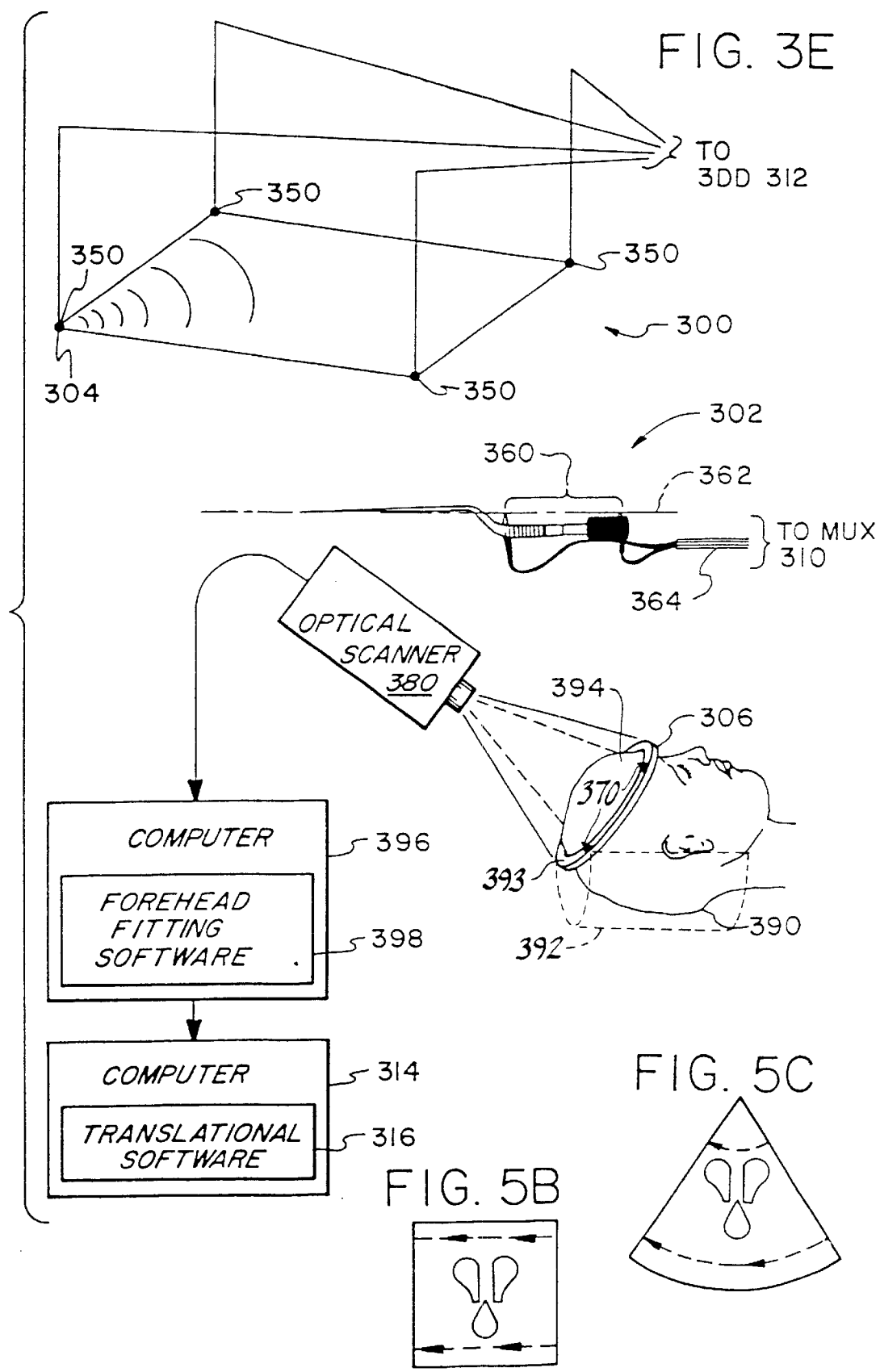

SYSTEM FOR DETERMINING THE POSITION IN A SCAN IMAGE CORRESPONDING TO THE POSITION OF AN IMAGING PROBE

This application is a continuation of U.S. patent application Ser. No. 09/151,798, filed Sep. 22, 1998, which is now U.S. Pat. No. 6,463,319, which is a continuation of U.S. patent application Ser. No. 08/543,516, filed Oct. 16, 1995, which is now U.S. Pat. No. 5,851,183, which is a continuation of U.S. patent application Ser. No. 07/858,980, filed May 15, 1992, now abandoned, which was a continuation-in-part of U.S. patent application Ser. No. 07/600,753, filed Oct. 19, 1990, now abandoned.

BACKGROUND OF THE INVENTION

Precise localization of position has always been critical to neurosurgery. Knowledge of the anatomy of the brain and specific functions relegated to local areas of the brain are critical in planning any neurosurgical procedure. Recent diagnostic advances such as computerized tomographic (CT) scans, magnetic resonance imaging (MRI) scanning, and positron emission tomographic (PET) scanning have greatly facilitated preoperative diagnosis and surgical planning. However, the precision and accuracy of the scanning technologies have not become fully available to the neurosurgeon in the operating room. Relating specific structures and locations within the brain during surgery to preoperative scanning technologies has previously been cumbersome, if not impossible.

Stereotactic surgery, first developed 100 years ago, consists of the use of a guiding device which channels the surgery through specific parts of the brain as localized by preoperative radiographic techniques. Stereotactic surgery was not widely used prior to the advent of modern scanning technologies as the injection of air into the brain was required to localize the ventricles, fluid containing chambers within the brain. Ventriculography carried a significant complication rate and accuracy in localization was marginal.

SUMMARY OF THE INVENTION

It is an object of this invention to provide a system which can determine the position of a probe within a head and display an image corresponding to the determined position.

The invention comprises a system for determining a position of a tip of a probe, which is positioned within an object, relative to cross sectional images of the object. The system comprises measuring means, translating means and selecting and displaying means. The measuring means measures the position of the tip of the probe relative to the object. The translating means translates the position of the tip of the probe relative to the object into a coordinate system corresponding to the cross sectional images of the object. The selecting and displaying means selects the image of the object which corresponds to the measured position of the tip of the probe relative to the object and displays the selected image.

The invention also comprises a system for determining a position of a tip of a surgical probe, which is positioned within a head of a body of a patient, relative to cross sectional images of the head. Means measures the position of the tip of the surgical probe relative to the head. Means translates the position of the tip of the surgical probe relative to the head into a coordinate system corresponding to the cross sectional images of the head. Means selects the image of the head which corresponds to the measured position of the tip of the surgical probe relative to the head and displays the selected image.

The invention also comprises a method for determining a position of a tip of a surgical probe, which is positioned within a head of a body of a patient, relative to cross sectional images of the head, said method comprising the steps of: measuring the position of the tip of the surgical probe relative to the head; translating the position of the tip of the surgical probe relative to the head into a coordinate system corresponding to the cross sectional images of the head; selecting the image of the head which corresponds to the measured position of the tip of the surgical probe relative to the head; and displaying the selected image.

The invention also comprises a system for determining a position of an ultrasound probe relative to a head of a body of a patient when the probe is positioned adjacent to the head. An array is positioned adjacent the probe. First means determines the position of the ultrasound probe relative to the array. Second means determines the position of the head relative to the array. Means translates the position of the ultrasound probe into a coordinate system corresponding to the position of the head.

Other objects and features will be in part apparent and in part pointed out hereinafter.

BRIEF DESCRIPTION OF THE DRAWINGS

FIG. 3D is a perspective schematic diagram of an optical scanner used in combination with a cradle.

FIG. 3E is a perspective schematic diagram of the microphone array, surgical probe, base ring and optical scanner according to the invention.

FIG. 5A is a perspective schematic diagram of an ultrasound probe system according to the invention.

FIGS. 5B and 5C illustrate scanned and ultrasound images, respectively.

Corresponding reference characters indicate corresponding parts throughout the several views of the drawings.

DETAILED DESCRIPTION OF THE PREFERRED EMBODIMENTS

With the advent of modern scanning equipment and techniques, several stereotactic systems have been developed and are presently available. These stereotactic systems allow a surgeon to localize specific points detected on CT, MRI or PET scans which have been previously generated prior to the surgical procedure being performed. In particular, the stereotactic systems allow the selection of specific points detected on the scans to be localized within the brain by the surgeon during the surgical procedure using a mechanical device.

Figure 1A:
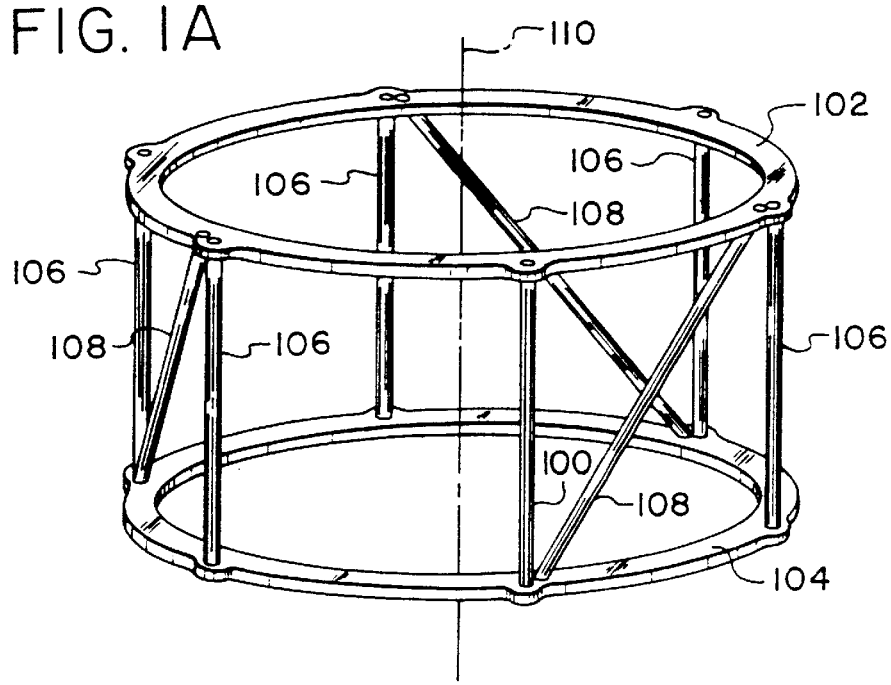
FIG. 1A is a perspective illustration of a cylindrical frame structure which is mounted around a patient's head during the scanning process.
Figure 1B:
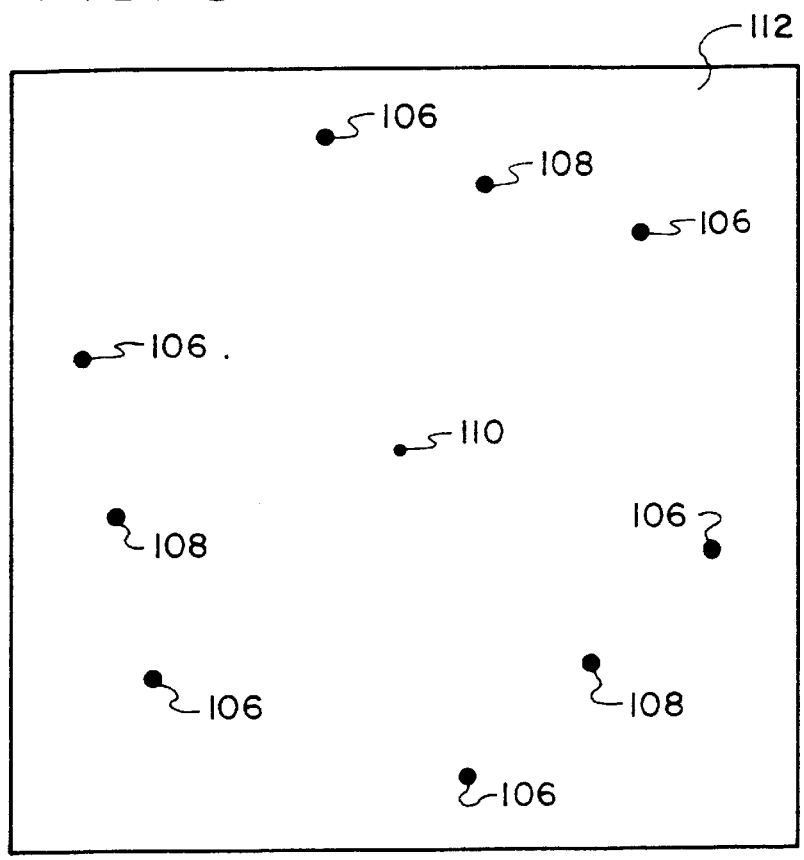
FIG. 1B is a plan view of the rods of the cylindrical frame structure of FIG. 1A taken along a plane midway between the upper and lower rings.

Initially, prior to the operative procedure, some form of localizing device, such as a frame, is attached to the patient's skull using sharp pins. The particular scan or scans which are to be performed are then generated with the head of the patient encircled by the frame. For example, the frame may be comprised of a cylindrical structure 100 as illustrated in perspective in FIG. 1A. Structure 100 includes an upper circular ring 102 and a lower circular ring 104 which are interconnected by six vertical rods 106 and three diagonal rods 108. The three diagonal rods 108 diagonally interconnect rings 102 and 104 so that any plane which passes through the cylindrical structure 100 and orthogonally intersects its axis 108 will intersect each of the diagonal rods 108 at a particular point. The resultant spacing between the diagonal and upright rods defines a unique plane within the cylindrical structure 100. For example, as shown in FIG. 1B, a scan in a particular plane would show a pattern of nine cross sectional views of the rods 106. The unique spacing of these views of the rods, as shown in plane 112 of FIG. 1B, would necessarily indicate that the position of the scan plane 112 was parallel to and midway between rings 102 and 104 of the cylindrical structure 100.

Figure 1C:
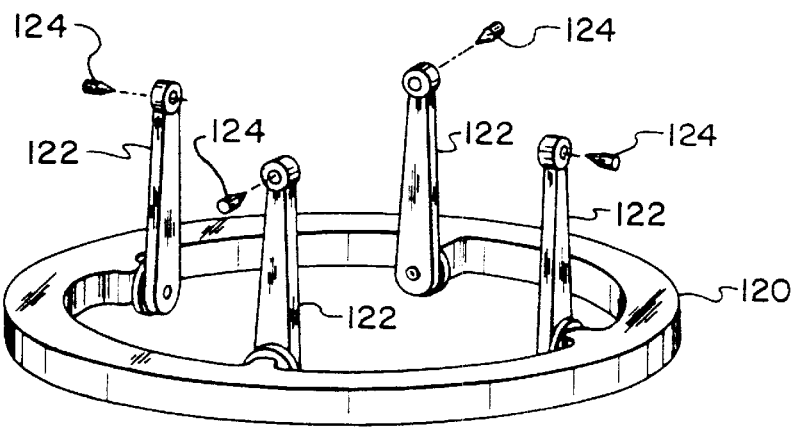
FIG. 1C is a perspective illustration of a reference ring which is mounted by uprights to a patient's head to support the cylindrical frame structure of FIG. 1A.

As a result of the scanning process, the images obtained are analyzed and the position within the images of the specific marking rods 106, called fudicels, are identified and measured. By measuring the distance between the rods 106, the specific location of a scan with reference to a base plane can be identified. Generally, the lower ring 104 of the cylindrical structure 100 is attached to a reference ring 120 (also known as a BRW head ring) as illustrated in FIG. 1C. As noted above, this ring 120 is supported on the patient's head via uprights 122 attached to the head by the use of sharp pins 124 so that the ring 120 is held firmly in place with respect to the head. The lower ring 104 of the cylindrical structure 100 is mounted to the reference ring 120 attached to the patient's head so that these two rings are in parallel planes.

Figure 1D:
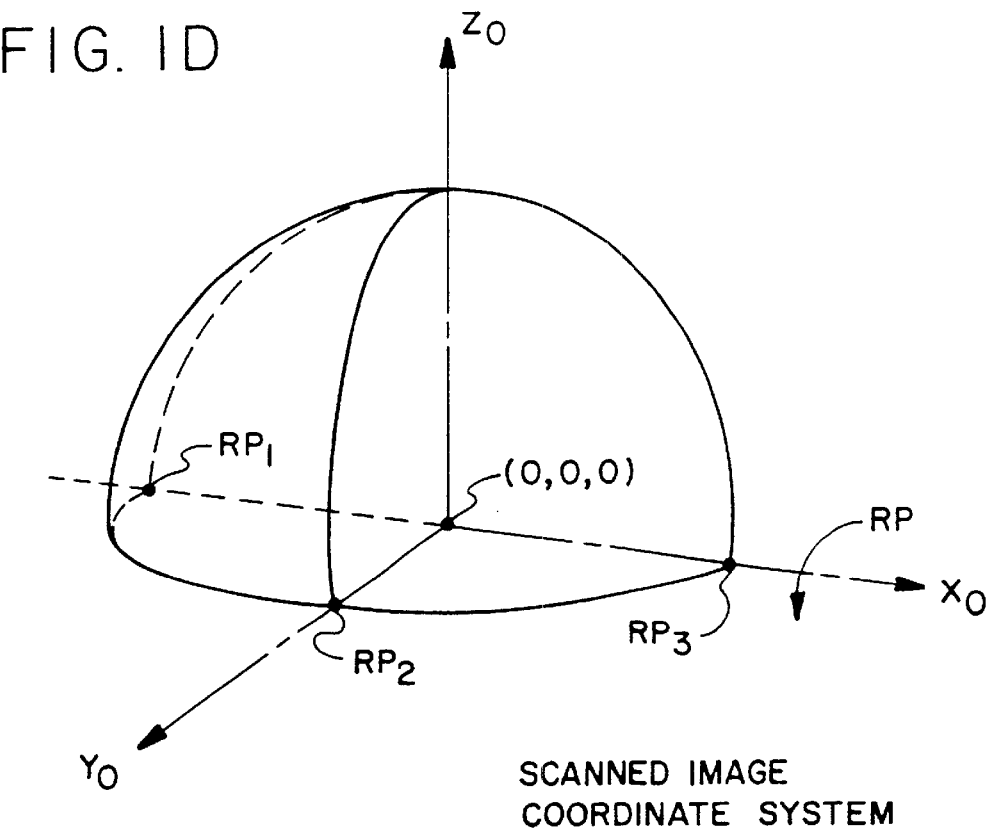
FIG. 1D is a perspective illustration of the coordinate system of a three dimensional scanned image.

As shown in FIG. 1D, the scanning system (e.g., CT, MRI, PET) which is performing the scanning has a scanned image coordinate system $(X_o, Y_o, Z_o)$ within which a reference plane RP can be defined by at least three reference points RP1, RP2 and RP3 located on the head 124 of the patient. A computer is then used to calculate a specific position within the brain and a target picked out on the specific image can be approached with a fair degree of accuracy during the surgical procedure.

Although stereotactic surgery allows a surgeon to be guided to a specific point with accuracy, it has not been particularly useful in allowing the surgeon to identify the particular location of a surgical probe within the brain at any point during the surgical process. Frequently in neurosurgery, brain tumors or other target points within the brain are indistinguishable from surrounding normal tissue and may not be detected even with the use of frozen sections. Moreover, with modern microsurgical techniques, it is essential that the neurosurgeon identify specific structures within the brain which are of critical functional importance to the patient. In addition, the boundaries of these structures must be accurately defined and specifically known to the surgeon during the surgical process. In this way, these tissues will not be disturbed or otherwise damaged during the surgical process resulting in injury to the patient.

Figure 2A:
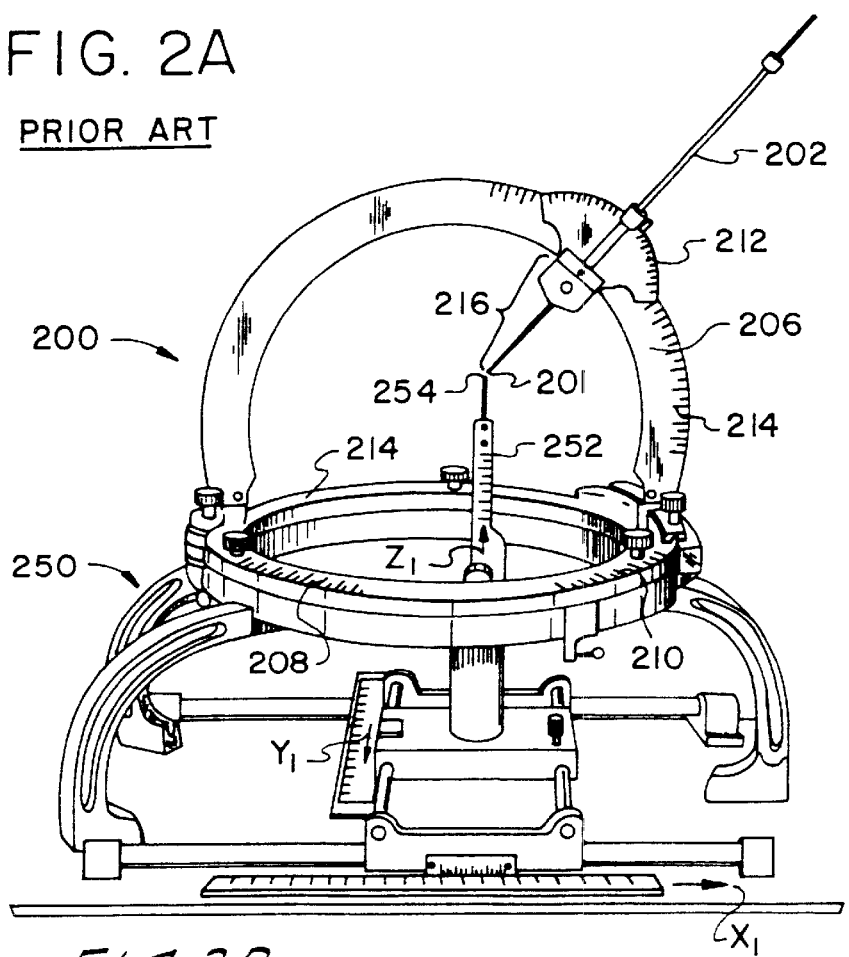
FIG. 2A is a perspective view of the caliper frame used to determine the relative position between a position in the head and the phantom base.
Figure 2B:
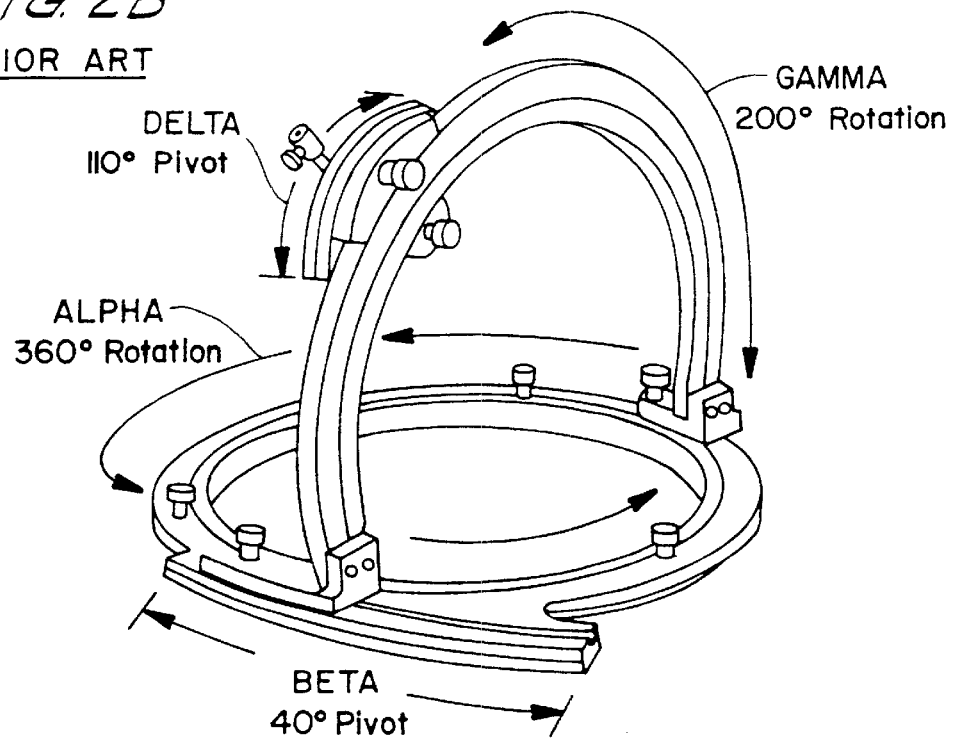
FIG. 2B is a perspective view of the caliper frame of FIG. 2A illustrating its angles of adjustment.

In the past, the surgeon has been able to use the stereotactic system in reverse in order to permit the determination of the position of a surgical probe relative to the scanned images so the image corresponding to the probe position can be identified and viewed. However, going in reverse from the patient's brain backwards to find the position of the surgical probe relative to the scan is a cumbersome and time-consuming process. Usually, a specially designed caliper frame 200, as illustrated in FIG. 2A, has to be attached to the ring 120 affixed to the patient's head to determine the position of the surgical probe in the head. For example, suppose the surgeon desires to know the position of a tip 201 of a probe 202 in the patient's head. First, the caliper frame 200 is fitted to the reference ring 120 affixed to the patient's head. Next, the position of probe 202 is positioned on arch 206 and the frame 200 is set to indicate the alpha, beta, gamma and delta angles on scales 208, 210, 212 and 214 that the probe 202 defines with respect to the frame 200, as shown in FIG. 2B. Next, the distance 216 from the tip of the probe 202 to the arch 206 is determined.

The caliper frame 200 is then transferred and mounted to a phantom base 250 in a manner as illustrated in FIG. 2A. The phantom base 216 has a coordinate system $(X_1, Y_1, Z_1)$. Generally, the caliper frame 200 identifies a point 201 over the phantom base 250. A pointing device 252 is positioned to have its tip 254 at point 201. The $X_1$–$Y_1$ plane of the phantom base 200 corresponds to a plane parallel to the plane in which the reference points RP1, RP2 and RP3 are located. The $(X_1, Y_1, Z_1)$ coordinates define the position of point 201. As a result, the position of point 254 with respect to the $X_1$–$Y_1$ plane and, therefore, with respect to the reference plane RP is now known. A computer can now be used to calculate the specific position within the brain and the particular scan which corresponds to the calculated position can now be accessed and viewed on a scanning system.

Figure 2C:
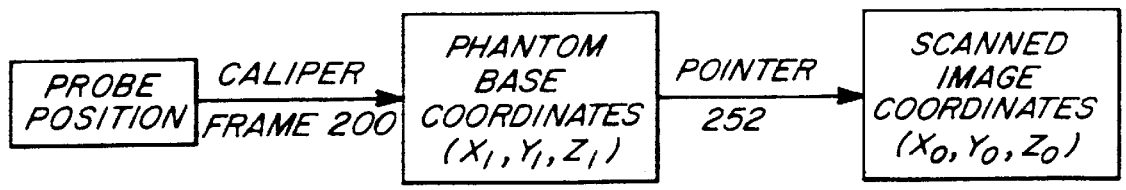
FIG. 2C is a block diagram of the steps involved in the prior art process of determining the position of surgical probe relative to the scanned images so that the image corresponding to the probe position can be identified and viewed by the surgeon.

In summary, this prior art process as shown in FIG. 2C identifies the location of the tip 201 of the surgical probe 202 for the surgeon. Initially, the surgeon positions the probe 202 on the caliper frame 200, which is attached to the head, at the position desired within the head. The caliper frame 200 is then removed from the patient's head and transferred to the phantom base 250. The pointing device 252 is then positioned at point 254 which is essentially coaxial with point 201 of the tip of the probe. The pointing device 252 then indicates the position of the tip of the probe in the phantom base coordinate system $(X_1, Y_1, Z_1)$. Finally, these coordinates are used to determine the scanned image coordinates ($X_o$, $Y_o$, $Z_o$) so that the image corresponding to the probe position can be displayed.

After this cumbersome and time-consuming process, the surgeon has now determined the position of the tip 201 of the probe 202 with respect to the scanned images and can now view the image corresponding to the probe position to decide the next step in the surgical procedure. This entire process takes approximately ten to fifteen minutes and increases the risks of intraoperative contamination as the base of the calipers are nonsterile. Because of these considerations, stereotactic surgery is not commonly employed in most procedures. Furthermore, the minimal accuracy it affords is generally insufficient for modern microsurgical techniques. Consequently, stereotactic surgery is not generally available to the majority of certain patients undergoing surgery.

Figure 2D:
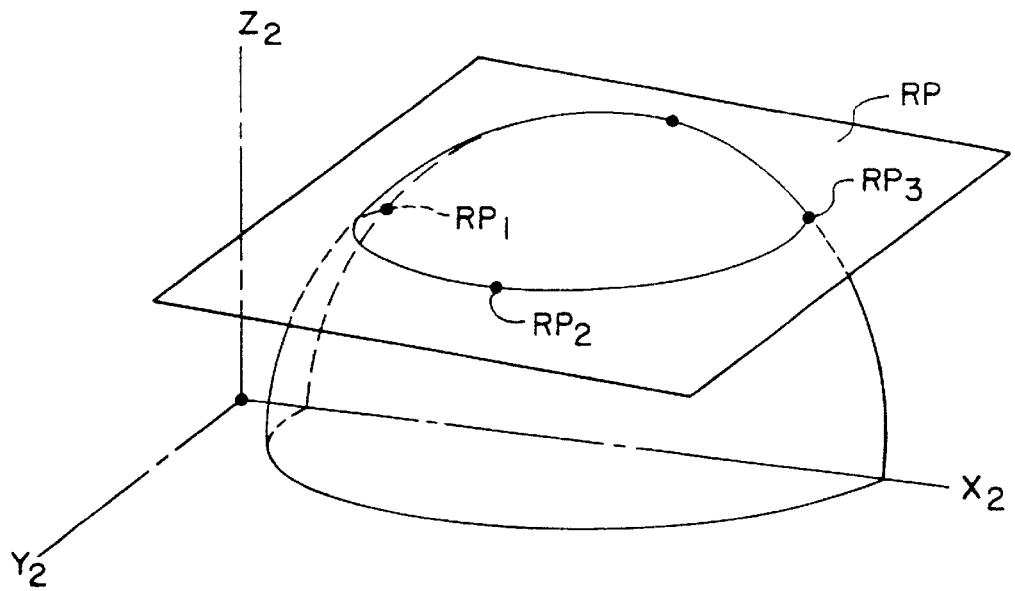
FIG. 2D is a perspective illustration of a three dimensional coordinate system of a surgical probe.

Comparing FIGS. 1D and 2A, it can be seen that it is necessary for the surgeon to know the specific location of the tip 201 of the surgical probe 202 with respect to the scanned image coordinate system ($X_o$, $Y_o$, $Z_o$) of the particular scans that were preoperatively performed. In other words, the surgical probe 202 has a particular coordinate system ($X_2$, $Y_2$, $Z_2$) which is illustrated in FIG. 2D. Ideally, the surgical probe coordinate system ($X_2$, $Y_2$, $Z_2$) must be related to the scanned image coordinate system ($X_o$, $Y_o$, $Z_o$). The prior art as illustrated in FIG. 2B has suggested relating these coordinate systems via the phantom base coordinate system ($X_1$, $Y_1$, $Z_1$). However, as noted above, this relational process is inaccurate, time-consuming and cumbersome. The invention uses a 3D digitizer system to locate the position of the tip 201 of the surgical probe 202 and to directly relate the surgical probe coordinate system ($X_2$, $Y_2$, $Z_2$) to the scanned image coordinate system ($X_o$, $Y_o$, $Z_o$).

Figure 3A:
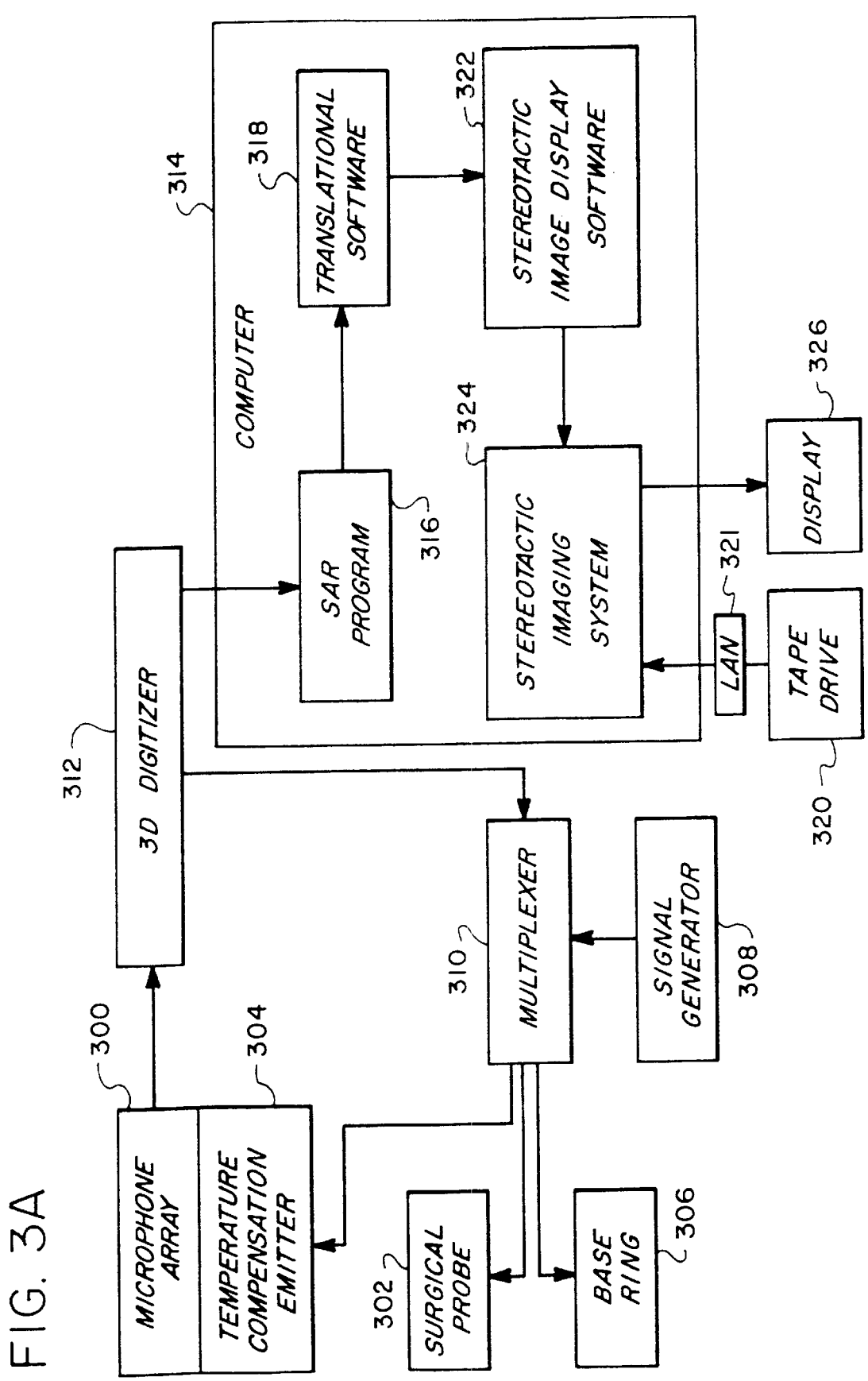
FIG. 3A is a block diagram of a system according to the invention for indicating the position of a surgical probe within a head on an image of the head.
Figure 3B:
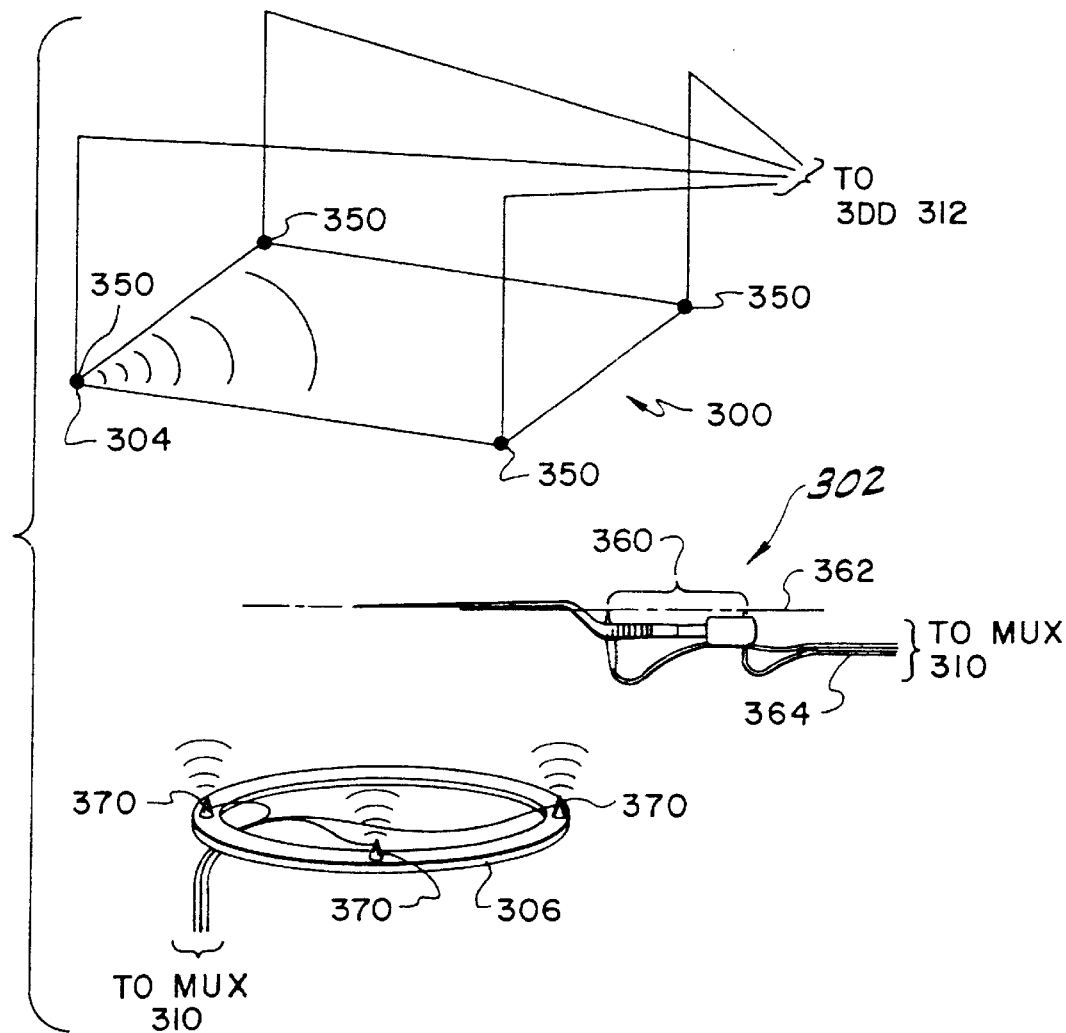
FIG. 3B is a perspective schematic diagram of the microphone array, surgical probe and base ring according to the invention.

In particular, an off-the-shelf, three dimensional sonic digitizer such as Model GP-8-3D produced by Scientific Accessories Corporation is used to determine the position of the probe. As shown in FIG. 3A, the 3D digitizer system includes a microphone array 300 which is generally mounted in the operating room on the ceiling or in some other position so that it is in a line of sight with the surgical probe 302 that is being used. As will be described in greater detail below, the probe 302 includes transmitters such as sound emitters thereon which interact with the microphone array 300 so that the position of the tip of surgical probe 302 is known at any particular instant in time. The 3D digitizer system also includes a temperature compensation emitter 304 associated with the microphone array 300. Furthermore, mounted to the ring 120 (FIG. 1C) affixed to the patient's head is a base ring 306 which is coaxial and parallel with the plane defined by reference ring 120. This base ring 306 includes a plurality of transmitters as will be described below which interact with the microphone array 300 so that the relative position of the base ring 306 can be determined any particular instant in time. Signal generator 308 generates a signal which is provided through a multiplexer 310 to the temperature compensation emitter 304, surgical probe 302, and base ring 306. Usually, temperature compensation emitter 304 is activated by the signal generator 308 via multiplexer 310 to emit a signal which is received by the microphone array 300. Each of the signals received by each of the microphones of the array 300 is provided to a digitizer 312 which digitizes the signals and provides the digitized signals to computer 314 which includes a spatial acquisition and recording (SAR) program 316 which acquires and records spatial coordinates based on the digitized signals. For example, program 316 may be the SACDAC program licensed by PIXSYS of Boulder, Colorado. This program evaluates the digitized signals emitted by the temperature compensation emitter 304 to determine the reference standards. i.e., the velocity of the radiation through the air. For example, depending on the temperature of the air in the operating room, the period of time that it takes from the instant that the temperature compensation emitter 304 is actuated to radiate a signal until the instant that each of the microphones of the array 300 receives the emitted signal will vary. The SAR program 316 knows, through calibration, the distance between the temperature compensation emitter 304 and each of the micro-phones of the array 300. Therefore, the SAR program 316 can immediately calculate the velocity of the signals being transmitted. This velocity establishes a reference for determining the position of the surgical probe 302 and the base ring 306.

Next, the emitters of the base ring 306 are activated so that the position of the base ring 306 can be determined. At this point, the emitters of the base ring 306 are successively energized and the radiation transmitted by these emitters is detected by the microphone array 300. The signal generated by the microphones from this radiation is digitized and evaluated by the SAR program 316 to determine the position of each of the emitters of the base ring 306. Once the positions of the base ring emitters have been determined by the SAR program 316, standard geometrical computations are performed by the SAR program to determine the plane defined by the base ring 306 with respect to the microphone array 300.

Digitizer 312 then signals multiplexer 310 to provide the signal generated by signal generator 308 to the surgical probe 302. At this point, the emitters of the surgical probe 302 are successively energized and the radiation transmitted by these emitters is detected by the microphone array 300. The signal generated by the microphones from this radiation is digitized and evaluated by the SAR program 316 to determine the position of each of the emitters of the surgical probe 302. Once the positions of the probe emitters have been determined by the SAR program 316, standard geometrical triangulation is performed by the SAR program to determine the location of the tip of the surgical probe with respect to the microphone array 300.

Therefore, by using the 3D digitizer system, the position of the base ring 306 and the position of the surgical probe 302 relative to the base ring 306 can be determined by the SAR program 316. As noted above, the base ring 306 is mounted to the reference ring 120 (FIG. 1C) and is essentially coplanar therewith so that the base ring 306 defines the reference plane RP of the scanned image coordinate system illustrated in FIG. 1D.

Computer 314 includes translational software 318 which then translates the coordinates of surgical probe coordinate system illustrated in FIG. 2D into the scanned image coordinate system illustrated in FIG. 1D. As a result of this translation, computer 314 has now determined the particular scanned image of the preoperative scan on which the tip of the surgical probe 302 would be located. The system includes a tape drive 320, accessed through a local area network (LAN) 321, in which each of the images of the preoperative scan are stored. The translated coordinates generated by translational software 318 are provided to the stereotactic image display software 322, also resident within computer 314, and identify the particular scanned image which is to be viewed by the surgeon. The identified image is selected by the stereotactic imaging system 324 which recreates the image from the data stored in tape drive 320 and displays it on a high resolution display 326. Stereotactic image display software 322 and stereotactic image system 324 may be any off-the-shelf system such as manufactured by Stereotactic Image Systems, Inc. of Salt Lake City, Utah.

Referring to 3B, a perspective illustration of the microphone array 300, temperature compensation emitter 304, surgical probe 302 and base ring 306 are illustrated. Microphone array 300 includes a plurality of microphones 350, the outputs of which are connected to 3D digitizer 312. Adjacent to the microphone array 300 is a temperature compensating emitter 304 which selectively emits signals used by the SAR program in calibration to determine the velocity of the radiation. For example, in the Scientific Accessories Corporation Model GP-8-3D, a sonic digitizer is used. In this case, the speed of sound being transmitted from the temperature compensation emitter 304 to the microphones 350 is calculated by the SAR program to determine the speed at which the sound is being transmitted through the air. Since this system is very accurate and the speed of sound varies fairly significantly with respect to the temperature of the air, the temperature compensation emitter 304 allows the 3D digitizer system to compensate for changes in the air temperature in the operating room. Surgical probe 302 comprises a bayonet surgical forceps modified to carry at least two sound emitters thereon which are essentially coaxial on axis 362 with the tip of the forceps. The emitters are in line and immediately below the surgeon's line of sight through the forceps so that the line of sight is not blocked. In general, the microphone array 300 is attached to the operating light above the patient's head so that it is in direct line of sight with the forceps as they are being used by the surgeon. The microphones 350 listen to the sound emitted from the sequential energization of the emitters 360 on the forceps. The SAR software 316 measures the time of transmission from each of the sound emitters 360 on the forceps to the microphones 350. By comparing these times, the position of both emitters 360 and, therefore, the tip of the forceps can be calculated by the SAR program 316.

Base ring 306 is affixed to the reference ring 120 attached to the patient's head and is essentially coplanar with the reference points RP1, RP2 and RP3. Base ring 306 includes a plurality of emitters 370 thereon which are connected to multiplexer 310 and energized by signal generator 308. Each one of these emitters 370 is sequentially energized so that the radiation emitter thereby is received by the microphones 350 of array 300. The emitters 370 are preferably positioned 900 apart with the center emitter being located at the anterior of the head. This permits base ring 306 to be mounted around the head so that all three emitters are in line of sight with the array. The resulting signals are digitized by digitizer 312 so that the SAR program 316 is able to determine the plane in which the emitters 370 are located. This plane essentially defines the reference plane because it is coplanar with the reference points RP1, RP2 and RP3. By determining the position of the reference plane, translational software 318 is now able to take the coordinate position of the probe 302 and translate it from the surgical probe coordinate system of FIG. 2D into the scanned image coordinate system as illustrated in FIG. 1D. As a result, the particular scanned image which corresponds to the position of the probe can be identified and displayed for viewing by the surgeon.

The surgical probe 302 is generally a bayonet cauterizing device which has a bundle of wire 364 attached thereto. Therefore, the wires required to connect the emitters 360 to the multiplexer 310 are part of the bundle of wires 364 which connect the forceps to its electrical power source and the surgeon is familiar with handling such forceps connected to a wire bundle. Therefore, there is no inconvenience to the surgeon in using such a probe and the surgeon is familiar with handling such a forceps connected to a wire bundle.

Base ring 206 is one apparatus for determining and positioning the reference points RP1, RP2 and RP3 with respect to the microphone array 300. An advantage of the base ring 306 is that each time the patient's head is moved the base ring 306 is energized to define the reference plane. This allows the surgeon to move the patient's head during surgery. Alternatively, the reference points RP1, RP2 and RP3 can be established by using a reference mode of the 3D digitizer 312. In particular, the tip of probe 302 is positioned on each of the reference points RP1, RP2 and RP3 and actuated to emit a signal to the microphone array 300 so that the position of the tip can be determined at each of these points. This is performed during a reference mode of operation of the 3D digitizer 312 so that the SAR program 316 calculates, at the end of the execution of this mode, the position of the reference points RP1, RP2 and RP3. This requires that the reference points have to be reestablished before the position of the surgical probe is determined to avoid changes in the reference plane due to movement of the head. On the other hand, one advantage of this approach is that the use of the reference ring 120 may be eliminated. In particular, it is possible that the reference pins 122 can be permanently affixed to the skull of the patient. For example, these pins may be radiolucent surgical screws which are embedded in the patient's skull and which have radiopaque tips. These screws would be affixed to the patient's skull before surgery and before the preoperative scanning so the radiopaque tips would provide a constant reference during scanning and throughout the stereotactic surgical procedure. During the actual surgery, the probe would be used to indicate the position of each of the radiopaque tips before the probe position was determined. By eliminating the need for the reference ring 120, other advantages are also achieved. For example, generally the preoperative scanning must be done under anesthetic because the reference ring 120 interferes with intubation. Therefore, intubation must occur before the reference ring is affixed to the skull. By eliminating the need for the reference ring 120 and using surgical screws to identify the reference points RP1, RP2 and RP3, the preoperative scanning can be performed without the need for intubation and the anesthesia accompanying it. In one alternative embodiment, it is contemplated that the emitters 370 may each be separately mounted to a screw or other fixed structure positioned at one of the reference points.

Figure 3C:
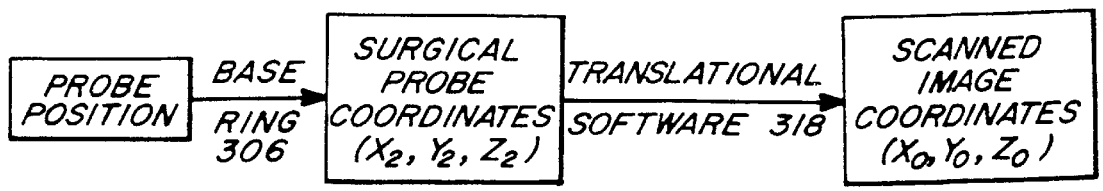
FIG. 3C is a block diagram of the steps involved in the process according to the invention for determining the position of a surgical probe relative to the scanned images so that the image corresponding to the probe position can be identified and viewed by the surgeon.

In summary, this process according to the invention is illustrated in FIG. 3C and identifies the location of the tip of the surgical probe 202 for the surgeon. Initially, the reference plane is determined by energizing the base ring 306 or by positioning the probe 302 at the reference points (as described herein). Next, the surgeon positions the probe in the position desired within the head. The emitters of the probe are then energized so that the probe position is measured and determined in the surgical probe coordinate system $(X_2, Y_2, Z_2)$. Next, the translational software 318 converts the surgical probe coordinate system into the scanned image coordinate system $(X_o, Y_o, Z_o)$ so that the image corresponding to the probe position can be displayed.

Referring to FIG. 3D, a perspective illustration of a patient's head 390 in a cradle 392 during the scanning process is shown. As will be described below, optical scanner 380, having emitters 381 thereon, is employed to determine the position of the head 390 relative to a cradle 392 positioned on the head.

Referring to 3E, a perspective illustration of the microphone array 300, temperature compensation emitter 304, surgical probe 302 and optical scanner 380 are illustrated.

Microphone array 300 includes a plurality of microphones 350, the outputs of which are connected to 3D digitizer 312. The microphone array 300 provides a fixed frame of reference to which the position of probe 302 is measured and to which the position of the head 390, relative to the cradle 392, is measured. As a result, the position of the probe 302 relative to the head 390 at any instant in time can be determined.

Adjacent to the microphone array 300 is a temperature compensating emitter 304 which selectively emits signals used by the SAR program in calibration to determine the velocity of the radiation. For example, in the Scientific Accessories Corporation Model GP-8-3D, a sonic digitizer is used. In this case, the speed of sound being transmitted from the temperature compensation emitter 304 to the microphones 350 is calculated by the SAR program to determine the speed at which the sound is being transmitted through the air. Since this system is very accurate and the speed of sound varies fairly significantly with respect to the temperature of the air, the temperature compensation emitter 304 allows the 3D digitizer system to compensate for changes in the air temperature in the operating room.

Surgical probe 302 comprises a bayonet surgical forceps modified to carry at least two sound emitters 360 thereon which are essentially coaxial on axis 362 with the tip of the forceps. The emitters are in line and immediately below the surgeon's line of sight through the forceps so that the line of sight is not blocked. In general, the microphone array 350 is attached to the operating room light above the patient's head so that it is in direct line of sight with the forceps as they are being used by the surgeon. The microphones 350 listen to the sound emitted from the sequential energization of the emitters 360 on the forceps. The SAR software 316 measures the time of transmission from each of the sound emitters 360 on the forceps to the microphones 350. By comparing these times, the position of both emitters 360 and, therefore, the tip of the forceps can be calculated by the SAR program 316.

Optical scanner 380 is generally located over the patient's head 390 and is used during scanning to establish the position of the head 390 relative to the cradle 392 thereby to relate the frame of reference of the cross sectional scans to the forehead 394. Scanner 380 is also used during surgery to establish the position of the head 390 relative to the cradle 392 thereby to relate the frame of reference of the probe 302 to the forehead 394.

During the preoperative scanning process as shown in FIG. 3D, when the cross sectional images of the head are created, the patient's head lies temporarily in cradle 392. The cradle includes an arc 393 of radiopaque material so that it appears in at least some of the cross sectional scans. As a result, the arc 393 defines a plane relative to the head 390. During scanning, this plane can be defined as the 0,0,0 plane for convenience. After the head is placed in the cradle, optical scanner 380 is used to establish the position of the cradle 392 and its attached arc 393 relative to the forehead 394. In particular, the optical scanner 380 scans both the forehead and the arc 393 of the cradle 392 and, via computer 396 employing forehead fitting software 398, determines the position of the arc 393 of the cradle 392 relative to the forehead 394. The forehead fitting software may be any off-the-shelf or custom software which graphs a set of points so that a curve defining the contour of the forehead can be calculated, a curve defining the arc can be calculated, and a curve defining the relative position of the forehead and the arc can be calculated. Since the position of the cross sectional scans relative to the radiopaque arc 393 is known (because the cradle arc defines the 0,0,0 plane) and since the position of the arc 393 of the cradle 392 relative to the forehead 394 is known (because of the scanning by the optical scanner), then the position of the cross sectional scans relative to the forehead is known and can be calculated by translational software 318.

During surgery, a base ring 306 is firmly affixed to the head. The base ring 306 does not have to be positioned in the same location relative to the head as the arc was during the scanning process when the cross sectional images were created. The base ring 306 used during surgery includes emitters 370 which communicate with the array 300 to establish the position of the base ring 306. As a result, the base ring 306 defines a plane relative to the head 390. After affixing the base ring to the head, optical scanner 380 is used prior to or during the surgery to establish the position of the base ring 306 relative to the forehead 394. In particular, the optical scanner 380 scans both the forehead and the base ring 306 and, via computer 396 employing forehead fitting software 398, determines the position of the base ring 306 relative to the forehead 394.

Since the position of the probe relative to the base ring is known (because of communication via the array) and since the position of the base ring relative to the forehead is known (because of the scanning by the optical scanner), then the position of the probe relative to the forehead is known and can be calculated by translational software 318. Since the position of the cross sectional images relative to the forehead is also known (from the preoperative scanning process), the end result is that the position of the probe relative to the cross sectional images is known so that the position of the tip of the probe on the closest cross sectional image can be displayed.

Optical scanner 380 and computer 396 are a standard, off the shelf scanner used to scan an object to determine its three-dimensional shape. For example, a limb scanner such as PIXSYS Optical Scanner used to develop three-dimensional models for artificial limbs may be used. The scanner 380 emits a laser beam or other optical beam toward the arc 393 and the forehead 394 and receives the light reflected there through an array of linear chip cameras such as CCD (charge coupled device) cameras. By evaluating the position of the reflected light using the camera array, the optical scanner 380, including a computer 396, determines the shape and, thus, the contour of the forehead 394, the shape of the arc 393 of cradle 392 and the relative position of the forehead and the arc 393. Computer 396 indicates to the translational software 318 of computer 314, which is a part of the system as illustrated in FIG. 3A, the position of the probe 302 relative to the forehead 392. The translational software 318 then coverts this indicated position into the coordinate system of the cross sectional scanned images. As a result, the particular scanned image which corresponds to the position of the probe can be identified and displayed on display 326 (FIG. 3A) for viewing by the surgeon.

The surgical probe 302 is generally a bayonet cauterizing device which has a bundle of wire 364 attached thereto. Therefore, the wires required to connect the emitters 360 to the multiplexer 310 are part of the bundle of wires 364 which connect the forceps to its electrical power source. Surgeons are generally familiar with handling such forceps connected to a wire bundle. Therefore, there is no inconvenience to the surgeon in using such a probe and the surgeon is experienced with handling such a forceps connected to a wire bundle.

One advantage of the optical scanner 380 is that it eliminates the need for a ring or pins to be attached to the patient's head during the preoperative scanning process. Each time the patient's head is placed in a cradle, the optical scanner 380 can be used to scan the head and cradle to redefine their relative position without the need for any contact. The reference ring (i.e., arc) on the head is, therefore, temporary. By eliminating the need for a permanent reference ring 120 or reference pins RP1–RP3, other advantages are also achieved. For example, generally the preoperative scanning must be done under anesthetic because the reference ring 120 interferes with intubation or it must be done after pins are affixed to the head. Therefore, intubation must occur before the reference ring is affixed to the skull. By eliminating the need for the permanent reference ring 120 and/or reference pins, and by using the contour of the forehead to define a reference point, the preoperative scanning can be performed without the need for intubation and the anesthesia accompanying it.

In summary, during the preoperative scanning process the patient simply lies in a U-shaped cradle attached to the end of a CT or MRI table. Above the patient's face is an arc providing the reference plane. All scans are obtained with reference to and preferably parallel to this arc defining the reference or base plane. The optical scanner relates the forehead contour to this arc so that the relation of the forehead to the scans is known.

In the operating room, the patient's head is again scanned with the optical scanner but this time the arc over the patient's head is base ring 306. The reference emitters attached to the base ring define the operative reference system. Therefore, the forehead is again related to the base ring by the optical scanner to define a new reference system; this time the new reference system is the operating room. The computer then matches the forehead contours obtained in the operating room and the scanning room to relate the two reference systems. In effect, the forehead is a "bridge" between the reference system of the preoperative scanner and the reference system of the operating room.

The cradle does not have to appear in the actual scans. The primary purpose of the cradle is to keep the patient's head from moving so that all scans are obtained with the same relationship to the arc.

Figure 4:
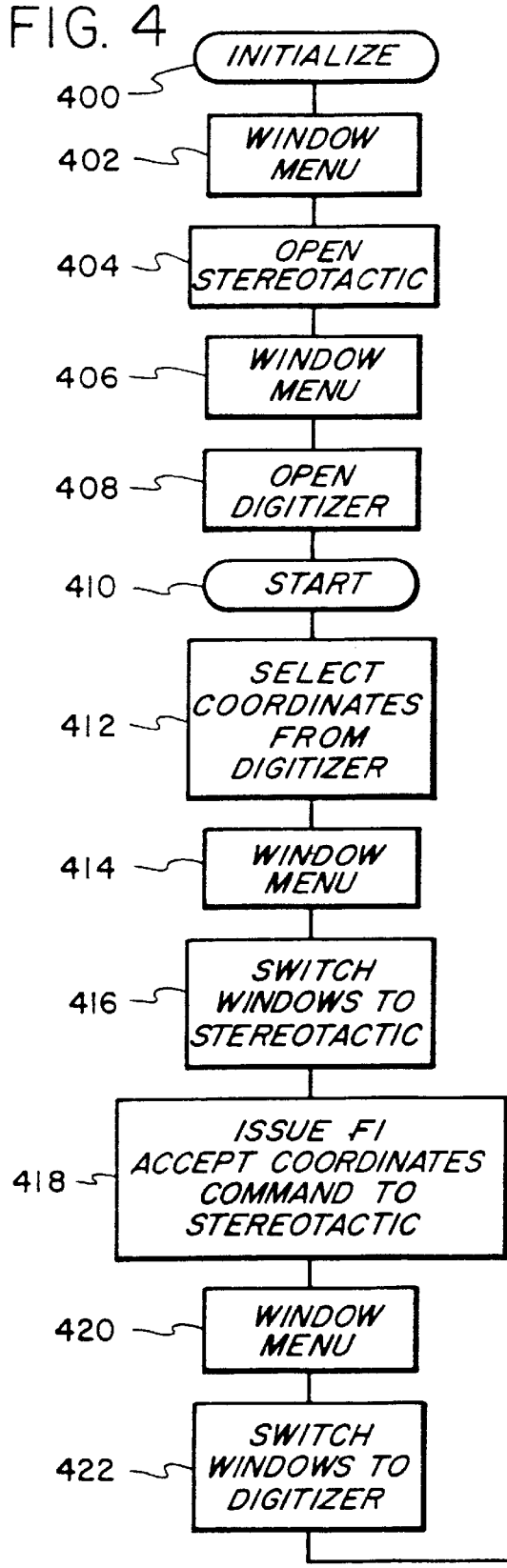
FIG. 4 is a flow chart of the translational software for translating coordinates from the surgical probe coordinate system to the scanned image coordinate system according to the invention.
Figure 4:
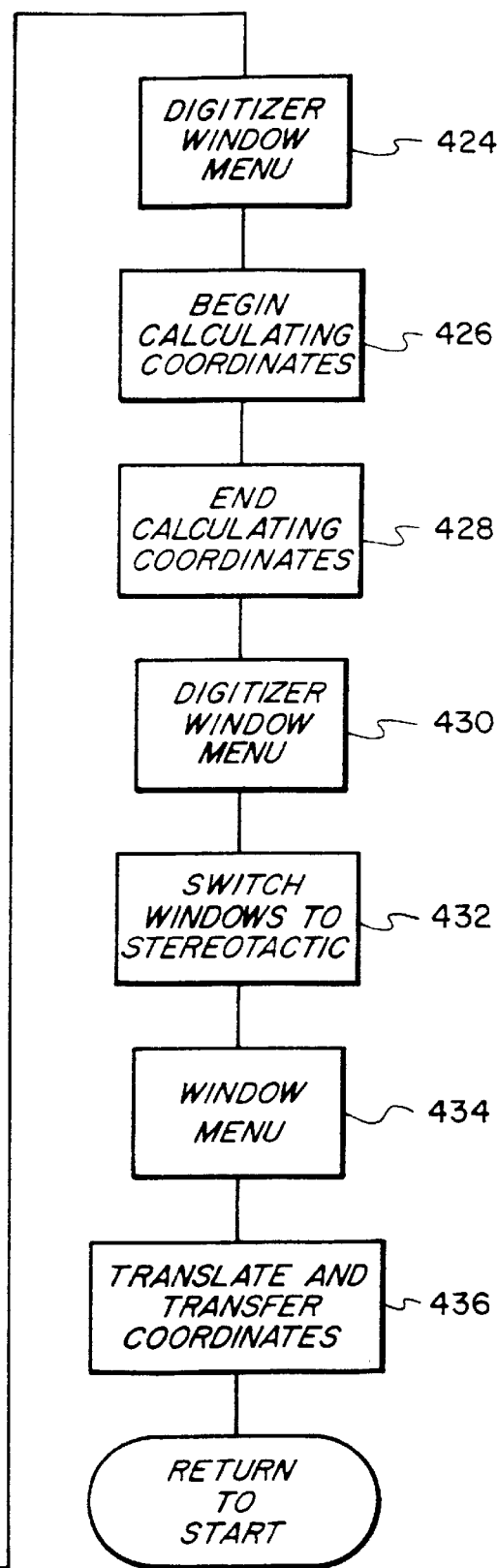

Referring to FIG. 4, a flow chart of the operation of the translational software 318 is illustrated. Initially, the surgeon locates the probe 302 in the position which is to be determined. (If a base ring 306 is not being used to identify the location of the reference plane, the initial step is for the surgeon to use the reference mode of the 3D digitizer 312 to identify the reference plane by locating the surgical probe tip at several points in the plane.)

The system initializes at step 400 so that translational software opens a window menu at step 402 of a multitasking program such as DESQ VIEW distributed by Quarterdeck Office Systems of Santa Monica, Calif. Such software permits simultaneous execution of multiple software programs. In general, once a program is selected for actuation, it continues to run either in the foreground or in the background until deactuated.

The translational software continues initializing by selecting the stereotactic imaging system and actuating the stereotactic imaging system in the foreground by opening the stereotactic window at step 404. Thereafter, the translational software returns to the window menu at step 406 moving the stereotactic image display software to the background and selects the digitizer window at step 408 to actuate the digitizer in the foreground. The computer is then ready to be actuated by the foot switch.

The surgeon then actuates a foot pedal or other switch which indicates that the system should perform a computation. Actuation of the foot switch is essentially the beginning of the start step 410. Upon actuation, the digitizer energizes calibration by the temperature compensation emitter 304 to determine the velocity of the sound waves, energizes the emitters of the base ring 306 to locate the reference plane and energizes the emitters of the surgical probe 302 to locate the position of the tip of the probe 302. The signals generated by the microphone array are digitized so that the SAR program 316 determines the coordinates of the tip of the surgical probe. At step 412, the translational software 318 selects the coordinates from the SAR program.

Next, the window menu is again accessed at step 414 and the window menu switches to the stereotactic image system software to the foreground at step 416 to specifically control the operation of the stereotactic imaging system 324. At this point, the translational software 318 issues an FI command to the stereotactic image display software 322 which in turn prepares the stereotactic imaging system 324 to accept coordinates. At step 420, the window menu is again selected so that at step 422 the computer switches the digitizer window into the foreground. At step 424, the digitizer window menu is accessed and coordinate translation is selected. At step 426, the digitizer begins calculating the coordinates and at step 428 the coordinate calculation is ended. The translational software then returns to the digitizer window menu at step 430, switches windows to place the stereotactic image system software in the foreground at 432 to prepare it for receiving the coordinates and again returns to the main window menu at step 434. Finally, the coordinate information is translated, including any necessary manipulation, and transferred to the stereotactic image display software 322 at step 436 which actuates the stereotactic imaging system 324 to select the particular image from the tape drive 320 and display it on high resolution display 326. The stereotactic image display software 322 instructs the stereotactic imaging system 324 to display the image closest to transferred coordinates and to display a cursor on the display 326 at the coordinates which corresponds to the position of the tip of the probe. Thereafter, the computer 314 is in a standby mode until the foot switch of the surgeon is again actuated to execute the translational software beginning with the start step 410.

The translation that occurs in step 436 depends on the position of the surgical probe coordinate system relative to the scanned image coordinate system and the units of measure. In the preferred embodiment, the systems are coaxial and the units of measure are the same so that algebraic adjustment is unnecessary. However, it is contemplated that the coordinates systems may not be coaxial, in which case translation would require arithmetic and/or trigonometric calculations. Also, the sequence, e.g., $(X_2, Y_2, Z_2)$, in which the coordinates are generated by the digitizer may be different than the sequence, e.g., $(X_o, Y_o, Z_o)$, in which stereotactic image system software receives coordinates. Therefore, the sequence in which the coordinates are transferred may have to be reordered.

Referring to FIG. 5A, a system employing an ultrasound localizer is illustrated. Reference character 500 refers to an ultrasound probe 500 which may be used in the operating room to scan the brain. The ultrasound probe 500 includes a plurality of at least three emitters 502 which communicate with the array 300 to define the plane in which the ultrasound probe 500 is scanning. Emitters 502 are energized via line 504 by multiplexer 310 as in the other systems illustrated above. The radiation emitted by emitters 502 is received by array 300 to determine the plane in which the ultrasound probe 500 is positioned. The ultrasound probe 500 is also connected via line 506 to a computer 508 which analyzes the ultrasound scanning and provides the analyzed information to a work station 510 which displays the scanned image. Since the array 300 can determine the position of the ultrasound probe 500 at any point in time, via digitizer 312, the particular plane of the image displayed on work station 510 is known. The position of the head 394 of the patient can be determined by attaching a base ring 306 with emitters 370 to the head, as noted above, or by scanning the forehead with an optical scanner 380 having emitters 381 thereon, as noted below.

For example, such an ultrasound image is illustrated in FIG. 5C. The surgeon can then call up the similar image on the display 326 of the stereotactic imaging system 324 such as illustrated in FIG. 5B. Alternatively, computer 508 may be linked to the stereotactic imaging system 324 directly to define the particular image plane illustrated on work station 510 so that display 326 can display the corresponding scanned image. As a result, the image from the ultrasound system, as illustrated on work station 510, is shown on one monitor and may be compared to a cross section to the images obtained either by CT, MRI or PET scanning. The cross section through the three dimensional data set as developed by the ultrasound system is determined by a high speed graphics work station, such as manufactured by Silicon Graphics. This allows the interpretation of the ultrasound scans as the anatomy from the MRI, CT or PET scans can be seen directly. Furthermore, the ultrasound system allows scanning in the operating room. Since the brain tissue is elastic and the position of various tissue may change from time to time, use of an ultrasound scan in the operating room permits a more definite localization of various brain tissues.

Alternatively, the system may be used for determining a position of the ultrasound probe relative to a head of a body of a patient. The probe 500 is positioned to scan the head 394 with an array 300 positioned adjacent the probe. At least three emitters 502 permit determination of the position of the ultrasound probe relative to the array. Optical scanner 380, having emitters 381 (FIG. 3D) permit determination of the position of the head relative to the array. Computer 396 translates the position of the ultrasound probe into a coordinate system corresponding to the position of the head.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A system comprising:
    a base fixed in relation to a subject;
    an imaging probe configured to scan the subject and provide scan images of the subject;
    an array of receivers in communication with the base and the imaging probe;
    a first plurality of reference points fixed in relation to the base, the first plurality of reference points in communication with the array;
    a second plurality of reference points fixed in relation to the imaging probe, the second plurality of reference points in communication with the array; and
    a processor in communication with the imaging probe and the array, wherein
    (i) the processor is configured to calculate a position of the first reference points relative to the array based on the communication between the first reference points and the array, thereby calculating a position of the base relative to the array, and calculating a position of the subject relative to the array;
    (ii) the processor is configured to calculate a position of the second reference points relative to the array based on the communication between the second reference points and the array, thereby calculating a position of the imaging probe relative to the array;
    (iii) the processor is configured to calculate a position of the imaging probe relative to the subject based on the calculated positions of the subject relative to the array and the imaging probe relative to the array; and
    (iv) the processor is configured to calculate the position in the scan images corresponding to the position of the imaging probe relative to the subject.

2. The system according to claim 1, further comprising a display in communication with the processor, wherein the processor is configured to generate images in the scan images corresponding to the position of the imaging probe relative to the subject and the display is configured to display scan images of the subject and the images corresponding to the position of the imaging probe relative to the subject.

3. The system according to claim 1, further comprising a signal generator located remotely from the imaging probe and the base and in communication with the imaging probe and the base, wherein the signal generator generates a signal and communicates that signal to the first and second reference points and wherein the first and second reference points communicate that signal to the receivers of the array.

4. The system according to claim 3, wherein the generator generates radiation signals communicated between the first reference points and the receivers of the array and between the second reference points and the receivers of the array.

5. The system according to claim 1, wherein the first and second reference points comprise emitters, the emitters communicating a signal to the receivers of the array.

6. The system according to claim 5, further comprising a signal generator located remotely from the imaging probe and the base and in communication with the imaging probe and the base, wherein the signal generator generates a signal and communicates that signal to the emitters and wherein the emitters communicate the signal to the receivers of the array.

7. The system according to claim 5, wherein the emitters are energizable to send a signal to the receivers of the array.

8. The system according to claim 1, further comprising a memory storing additional scan images of the subject, the scan images correlated to the subject, and wherein the processor is configured to calculate the position of the additional scan images corresponding to the position of the imaging probe relative to the subject.

9. The system according to claim 8, further comprising a display in communication with the processor, wherein the processor is configured to generate images in the scan images of the subject and the additional scan images of the subject corresponding to the position of the imaging probe relative to the subject and the display is configured to display images of the subject corresponding to the position of the imaging probe relative to the subject in the scan images and the additional scan images, wherein the scan images of the subject may be compared to the additional scan images of the subject.

10. The system according to claim 8, further comprising subject reference points located in fixed relation to the subject, wherein the subject reference points correlate the additional scan images to the subject.

11. The system according to claim 10, wherein the subject reference points comprise markers located in fixed relation to the subject, the markers identifiable in the additional scan images and the scan images.

12. The system according to claim 10, wherein the subject reference points comprise a subject contour which is representative of a contour of the subject, the subject contour identifiable in the additional scan images and the scan images.

13. The system according to claim 1, further comprising:
a light source positionable to direct light at the base and a surface of the subject; and
an array of sensors located remotely from the subject and positioned to receive light reflected from the base and the surface of the subject, the array of sensors in communication with the processor, and wherein the processor is configured to calculate the position of the subject relative to the array based on the light reflected to the array.

14. The system of claim 13, further comprising a memory storing previously taken scan images of the subject, the surface of the subject correlated to the previously taken scan images, and wherein the processor is configured to correlate the surface of the subject to the location of the surface of the subject in the previously taken scan images.

15. A system comprising:
a base fixed in relation to a body part;
a memory storing the first scan images of the body part in a first coordinate system, the location of the body part in the first coordinate system correlated to the first scan images;
an imaging probe configured to scan the body part and provide second scan images of the body part in a second coordinate system;
an array of detectors in communication with the base and the imaging probe;
a first plurality of reference points fixed in relation to the body part, the first plurality of reference points in communication with the array; and
a processor in communication with the array, wherein
(i) the processor is configured to determine the position of the first reference points in the second coordinate system, thereby determining the position of the body part in the second coordinate system;
(ii) the processor is configured to determine a corresponding position of the reference points in the second coordinate system, thereby determining the position of the imaging probe in the second coordinate system;
(iii) the processor is configured to determine the position in the second coordinate system corresponding to the position of the imaging probe relative to the body part, thereby determining the position of the imaging probe relative to the body part in the second scan images; and
(iv) the processor is configured to determine a plane in the first coordinate system corresponding to the position of the imaging probe relative to the body part in the second scan images, thereby determining the position of the imaging probe relative to the body part in the first scan images.

16. The system according to claim 15, wherein the processor is configured to generate images of the body part corresponding to the position of the imaging probe relative to the body part in the first and second coordinate systems and the first and second scan images.

17. The system according to claim 16, further comprising a display configured to display images of the body part corresponding to the position of the imaging probe relative to the subject in the first and second coordinate systems and the first and second scan images, wherein the images of the subject in the first and second scan images may be compared.

18. The system of claim 15, further comprising a second plurality of reference points fixed in relation to the imaging probe, the second plurality of reference points in communication with the array, wherein the processor is configured to determine the corresponding position of the second reference points in the second coordinate system, thereby determining the position of the imaging probe in the second coordinate system.

19. The system according to claim 18, further comprising a signal generator in communication with the imaging probe and the base, wherein the signal generator generates a signal and communicates that signal to the first and second reference points and wherein the first and second reference points communicate that signal to the detectors of the array.

20. The system according to claim 19, wherein the signal generator generates radiation signals communicated between the first reference points and the detectors of the array and between the second reference points and the detectors of the array.

21. The system according to claim 19, wherein the first and second reference points communicate radiation to the detectors of the array.

22. The system according to claim 18, wherein the first and second reference points comprise emitters, the emitters communicating a signal to the detectors of the array.

23. The system according to claim 22, wherein the emitters are energizable to send a signal to the detectors of the array.

24. The system according to claim 15, further comprising a reference fixed in relation to the body part and the base, the reference being identifiable in the first scan images of the first coordinate system.

25. The system according to claim 24, wherein the reference comprises a surface contour representative of a contour of the body part, the surface contour being identifiable in the first scan images of the first coordinate system.

26. The system according to claim 25, further comprising an optical scanner having a light source, the light source positionable to direct light at the base and the surface contour; and an array of sensors positioned to receive light reflected from the base and the contour surface and in communication with the processor, wherein the processor is configured to determine the position of the body part relative to the array based on the light reflected to the array.

27. The system according to claim 15, wherein the base comprises a ring and wherein the reference points are located on the ring.

28. The system according to claim 15, wherein the system further includes a surgical probe having an additional set of reference points in communication with the array and wherein the processor is configured to determine the position of the surgical probe in the second coordinate system and the second scan images and translate the determined position of the surgical probe in the second coordinate system into the corresponding position in the first coordinate system and the first scan images.

29. A system for determining a position relative to a body of a patient, the system comprising:

an array separate from the body of the patient;

body reference points fixed in relation to the body, the body reference points in communication with the array to communicate signals indicating the position of the body reference points;

a probe;

probe reference points fixed in relation to the probe, the probe reference points in communication with the array to communicate signals indicating the position of the probe reference points;

a memory having stored images of the body, the images including reference images correlatable to the body reference points; and a processor in communication with the array and the memory, the processor configured to determine the position of body and the probe based on communications from the body reference points and the probe reference points to the array and to translate the position of the body and the probe to the position of the body and the probe in the images of the body.

30. The system of claim 29, further comprising a display for displaying images of the body and the probe.

31. The system of claim 29 wherein the probe is an imaging probe capable of taking scan images of the body.

32. The system of claim 29 further including an imaging probe configured to scan the body providing scan images of the body, the imaging probe having imaging probe reference points fixed in relation to the imaging probe, the imaging probe reference points in communication with the array to communicate signals indicating the position of the imaging probe reference points.

* * * * *